(12) United States Patent
Devereux et al.

(10) Patent No.: US 11,464,946 B2
(45) Date of Patent: Oct. 11, 2022

(54) CHORDAE TENDINEAE MANAGEMENT DEVICES FOR USE WITH A VALVE PROSTHESIS DELIVERY SYSTEM AND METHODS OF USE THEREOF

(71) Applicant: MEDTRONIC VASCULAR, INC., Santa Rosa, CA (US)

(72) Inventors: Paul Devereux, Galway (IE); Paraic Frisby, Galway (IE); Frank White, Galway (IE); Tomas Kitt, Galway (IE); Marc Anderson, Galway (IE); Grainne Carroll, Galway (IE); Ciaran McGuinness, Roscommon (IE); Tim Jones, Galway (IE); Patrick Griffin, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 337 days.

(21) Appl. No.: 16/697,328

(22) Filed: Nov. 27, 2019

(65) Prior Publication Data
US 2020/0101268 A1 Apr. 2, 2020

Related U.S. Application Data

(62) Division of application No. 15/346,971, filed on Nov. 9, 2016, now Pat. No. 10,493,248.

(51) Int. Cl.
*A61F 2/24* (2006.01)
*A61M 25/10* (2013.01)
(Continued)

(52) U.S. Cl.
CPC ......... *A61M 25/10* (2013.01); *A61B 17/0218* (2013.01); *A61F 2/2427* (2013.01);
(Continued)

(58) Field of Classification Search
CPC ........ A61F 2/24; A61F 2/2427; A61F 2/2436; A61F 2/2466; A61B 2017/00783; A61M 25/10; A61M 25/1011
See application file for complete search history.

(56) References Cited

U.S. PATENT DOCUMENTS 5,370,685 A * 12/1994 Stevens ............... A61M 1/3653
623/2.11
5,916,193 A 6/1999 Stevens et al.
(Continued)

FOREIGN PATENT DOCUMENTS

EP 1472996 A1 11/2004
FR 2945440 A1 11/2010
(Continued)

OTHER PUBLICATIONS

The International Search Report and the Written Opinion of the International Searching Authority issued in International Application No. PCT/US2017/057695, dated Jan. 31, 2018.
(Continued)

*Primary Examiner* — Vi X Nguyen
(74) *Attorney, Agent, or Firm* — Medler Ferro Woodhouse & Mills PLLC

(57) ABSTRACT

Embodiments hereof relate to methods of delivering a valve prosthesis to an annulus of a native valve of a heart, the native valve having chordae tendineae. A chordae management catheter is positioned within a ventricle of the heart, the chordae management catheter having a displacement component at a distal end thereof. The displacement component has an annular shape and defines a central lumen therethrough. The displacement component is radially expanded to push chordae tendineae within the ventricle radially outward. A valve delivery system is introduced into the ventricle of the heart via a ventricular wall of the heart. The valve delivery system has the valve prosthesis at a distal
(Continued)

portion thereof. The valve delivery system is advanced through the central lumen of the radially expanded displacement component towards the annulus of the native valve of the heart. The valve prosthesis is deployed into apposition with the annulus of the native valve.

20 Claims, 29 Drawing Sheets

(51) Int. Cl.
    *A61B 17/02*     (2006.01)
    *A61M 25/04*     (2006.01)
    *A61B 17/00*     (2006.01)

(52) U.S. Cl.
    CPC ....... *A61F 2/2436* (2013.01); *A61M 25/1002* (2013.01); *A61M 25/1011* (2013.01); *A61B 2017/00557* (2013.01); *A61B 2017/00867* (2013.01); *A61B 2017/0237* (2013.01); *A61M 25/04* (2013.01); *A61M 2025/1072* (2013.01); *A61M 2025/1075* (2013.01); *A61M 2025/1079* (2013.01); *A61M 2025/1081* (2013.01)

(56) References Cited

U.S. PATENT DOCUMENTS

| | | | |
|---|---|---|---|
| 5,957,949 | A | 9/1999 | Leonhardt et al. |
| 6,277,136 | B1 | 8/2001 | Bonutti |
| 7,621,948 | B2 | 11/2009 | Herrmann et al. |
| 8,105,375 | B2 | 1/2012 | Navia et al. |
| 8,591,460 | B2 | 11/2013 | Wilson et al. |
| 9,034,032 | B2 | 5/2015 | Mclean et al. |
| 9,078,994 | B2 | 7/2015 | Rosenman et al. |
| 2004/0260394 | A1 | 12/2004 | Douk et al. |
| 2006/0265056 | A1 | 11/2006 | Nguyen et al. |
| 2007/0083082 | A1 | 4/2007 | Kiser et al. |
| 2007/0239266 | A1 | 10/2007 | Birdsall |
| 2007/0239269 | A1 | 10/2007 | Dolan et al. |
| 2008/0071369 | A1 | 3/2008 | Tuval |
| 2008/0306442 | A1 | 12/2008 | Bardsley et al. |
| 2010/0256749 | A1* | 10/2010 | Tran ............... A61F 2/2436 206/370 |
| 2011/0208297 | A1 | 8/2011 | Tuval et al. |
| 2012/0035722 | A1 | 2/2012 | Tuval |
| 2012/0059458 | A1 | 3/2012 | Buchbinder et al. |
| 2012/0078237 | A1 | 3/2012 | Wang et al. |
| 2012/0101572 | A1 | 4/2012 | Kovalsky et al. |
| 2012/0271411 | A1 | 10/2012 | Duhay et al. |
| 2013/0060328 | A1 | 3/2013 | Rothstein |
| 2013/0079872 | A1 | 3/2013 | Gallagher |
| 2013/0190861 | A1 | 7/2013 | Chau et al. |
| 2013/0226290 | A1 | 8/2013 | Yellin et al. |
| 2013/0231735 | A1 | 9/2013 | Deem et al. |
| 2013/0253571 | A1 | 9/2013 | Bates |
| 2013/0310928 | A1 | 11/2013 | Morriss et al. |
| 2014/0039611 | A1 | 2/2014 | Lane et al. |
| 2014/0056169 | A1 | 2/2014 | Jung et al. |
| 2014/0067049 | A1 | 3/2014 | Costello |
| 2014/0148889 | A1 | 5/2014 | Deshmukh et al. |
| 2014/0277404 | A1 | 9/2014 | Wilson et al. |
| 2014/0277405 | A1 | 9/2014 | Wilson et al. |
| 2014/0350660 | A1 | 11/2014 | Cocks et al. |
| 2014/0350669 | A1 | 11/2014 | Gillespie et al. |
| 2014/0371843 | A1 | 12/2014 | Wilson et al. |
| 2014/0379074 | A1 | 12/2014 | Spence et al. |
| 2015/0119981 | A1 | 4/2015 | Khairkhahan et al. |
| 2015/0238315 | A1 | 8/2015 | Rabito et al. |
| 2015/0289975 | A1 | 10/2015 | Costello |
| 2015/0297346 | A1 | 10/2015 | Duffy et al. |
| 2015/0305869 | A1 | 10/2015 | Styrc |
| 2015/0335424 | A1 | 11/2015 | Mclean et al. |
| 2016/0045350 | A1 | 2/2016 | Berra |
| 2016/0175565 | A1 | 6/2016 | Schaffer |
| 2016/0213470 | A1 | 7/2016 | Ahlberg et al. |
| 2016/0235531 | A1 | 8/2016 | Ciobanu et al. |

FOREIGN PATENT DOCUMENTS

| | | |
|---|---|---|
| JP | 2015530916 A | 10/2015 |
| JP | 2016512753 A | 5/2016 |
| WO | 2014015999 A1 | 1/2014 |
| WO | 2014144937 A2 | 9/2014 |

OTHER PUBLICATIONS

Office Action dated Sep. 17, 2021 in corresponding Japanese Patent Application No. 2019-523839.

* cited by examiner

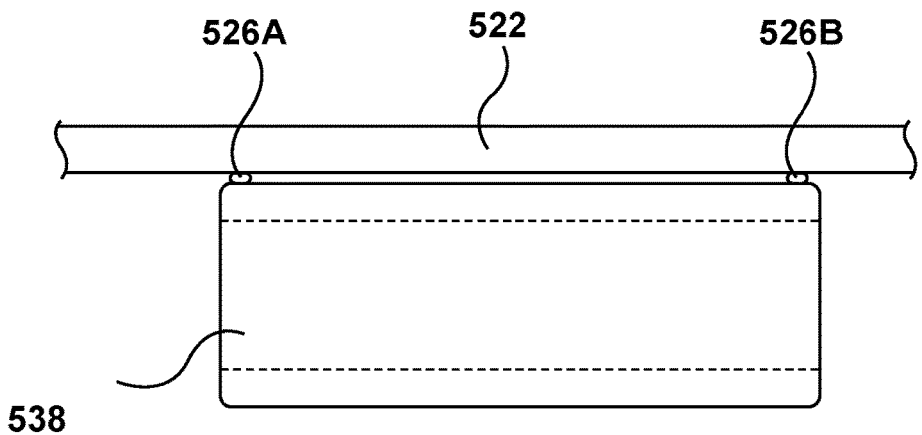
FIG. 6
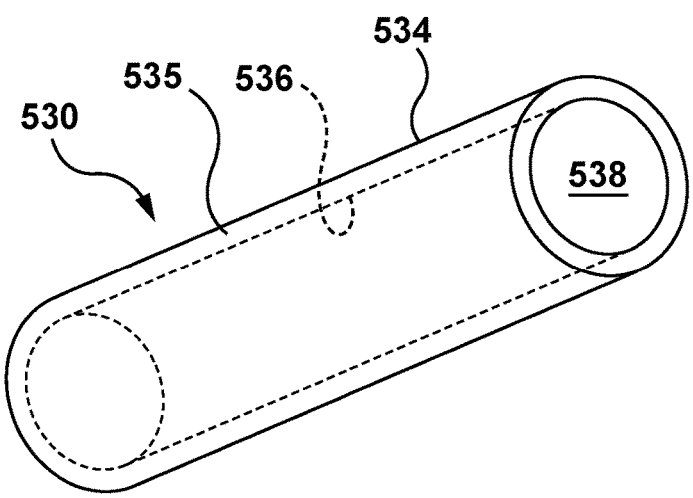
FIG. 7
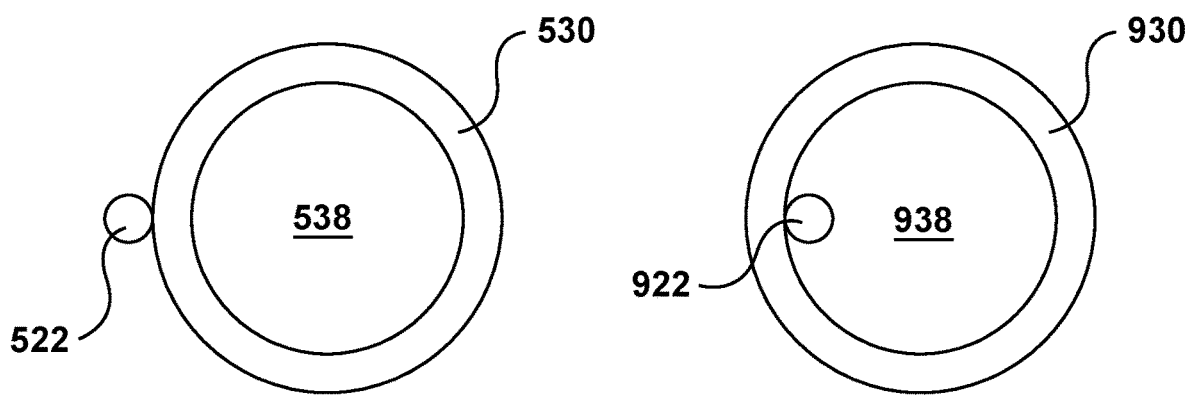
FIG. 8
FIG. 9

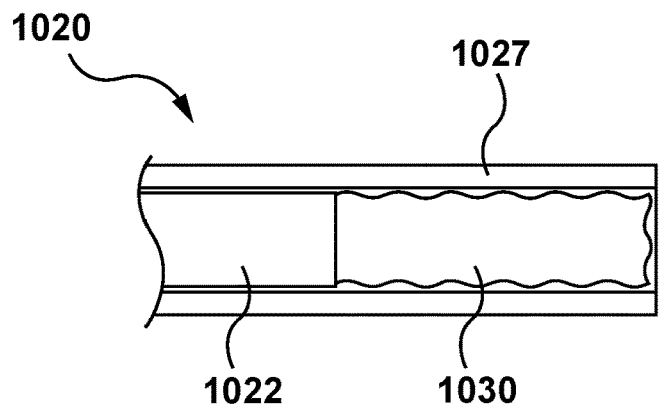
FIG. 10A
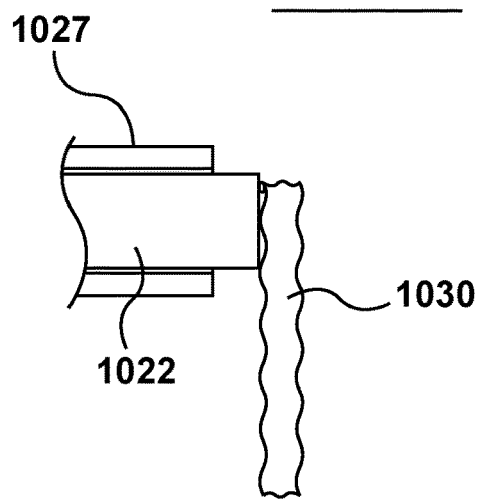
FIG. 10B
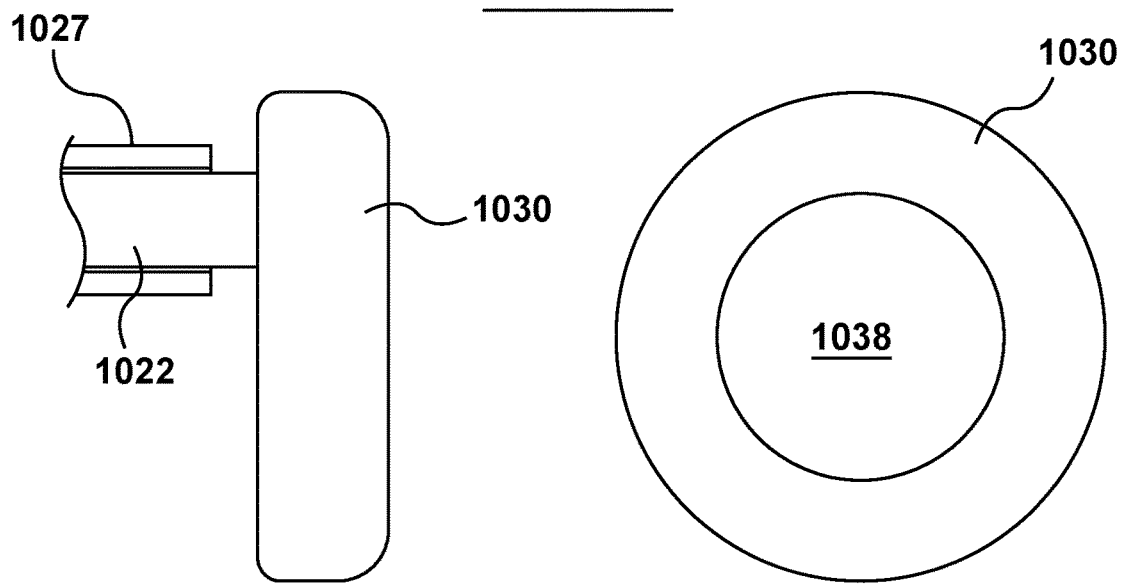
FIG. 10C
FIG. 10D

CHORDAE TENDINEAE MANAGEMENT DEVICES FOR USE WITH A VALVE PROSTHESIS DELIVERY SYSTEM AND METHODS OF USE THEREOF

CROSS-REFERENCE TO RELATED APPLICATION

This application is a divisional of U.S. application Ser. No. 15/346,971, filed Nov. 9, 2016, the disclosure of which is incorporated by reference herein in its entirety.

FIELD OF THE INVENTION

The invention relates to valve prostheses and more particularly to devices configured for use with a valve delivery system for managing chordae tendineae during delivery of valve prostheses in situ.

BACKGROUND OF THE INVENTION

A wide range of medical treatments are known that utilize "endoluminal prostheses." As used herein, endoluminal prostheses are intended to include medical devices that are adapted for temporary or permanent implantation within a body lumen, including both naturally occurring and artificially made lumens. Examples of lumens in which endoluminal prostheses may be implanted include but are not limited to arteries, veins, gastrointestinal tract, biliary tract, urethra, trachea, hepatic and cerebral shunts, and fallopian tubes.

Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets disposed within the interior of the stent structure. The prosthetic valve can be reduced in diameter, by being contained within a sheath component of a valve delivery system or by crimping onto a balloon catheter, and advanced through the venous or arterial vasculature. Once the prosthetic valve is positioned at the treatment site, for instance within an incompetent native or previously implanted prosthetic valve, the stent structure may be expanded to hold the prosthetic valve firmly in place. One embodiment of a prosthetic valve having a stent structure is disclosed in U.S. Pat. No. 5,957,949 to Leonhardt et al. entitled "Percutaneous Placement Valve Stent," which is incorporated by reference herein in its entirety.

A human heart includes two atrio-ventricular valves through which blood flows from the atria to the ventricles, the valves functioning to prevent return of blood to the atrium. The tricuspid valve, also known as the right atrio-ventricular valve, is a tri-flap valve located between the right atrium and the right ventricle. The mitral valve, also known as the bicuspid or left atrioventricular valve, is a dual-flap valve located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function. The mitral valve includes two moveable leaflets, an anterior leaflet and a posterior leaflet, that each open and close in response to differential pressures on either side of the valve. Ideally, the leaflets move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with mitral regurgitation or backflow typically having relatively severe physiological consequences to the patient.

Chordae tendineae extend within the left ventricle between the native leaflets of the mitral valve and the papillary muscles. Chordae tendineae are cord-like tendons that connect the medial papillary muscle to the posterior leaflet of the mitral valve and connect the lateral papillary muscle to the anterior leaflet of the mitral valve. One method of delivering a mitral valve prosthesis includes delivery via a transapical approach directly through the apex of the heart via a thoracotomy. However, during such a transapical approach, the chordae tendineae may act as an obstacle within the delivery pathway. Chordae tendineae are not all aligned the same way making the delivery pathway to the mitral valve more challenging. The valve delivery system may become entangled in chordae tendineae during advancement, thereby restricting movement of the valve delivery system within the anatomy and also preventing accurate alignment and/or deployment of the valve prosthesis.

Due to the different physical characteristics of the mitral valve compared to other valves, implantation of a valve in the mitral position has its own unique requirements for valve replacement. There is a continued desire to improve mitral valve replacement devices and procedures to accommodate the structure of the heart, including by providing improved devices and methods for replacing the mitral valve percutaneously. Embodiments hereof relate to methods and devices for managing chordae tendineae during a transapical valve replacement procedure.

BRIEF SUMMARY OF THE INVENTION

Embodiments hereof relate to methods of delivering a valve prosthesis configured for delivery within a vasculature. A method of delivering a valve prosthesis to an annulus of a native valve of a heart, the native valve having chordae tendineae. A chordae management catheter is positioned within a ventricle of the heart, the chordae management catheter having a displacement balloon at a distal end thereof. The displacement balloon is an annular component defining a central lumen therethrough. The displacement balloon is inflated within the ventricle to push chordae tendineae radially outward. A valve delivery system is introduced into the ventricle of the heart via a ventricular wall of the heart. The valve delivery system has the valve prosthesis at a distal portion thereof, wherein the valve prosthesis is in a delivery configuration. The valve delivery system is advanced through the central lumen of the inflated displacement balloon towards the annulus of the native valve of the heart. The valve prosthesis is deployed into apposition with the annulus of the native valve.

In another embodiment hereof, a method of delivering a valve prosthesis to an annulus of a native valve of a heart, the native valve having chordae tendineae. A chordae management catheter is positioned within a ventricle of the heart, the chordae management catheter having a displacement component at a distal end thereof. The displacement component has an annular shape and defines a central lumen therethrough. The displacement component is radially expanded to push chordae tendineae within the ventricle radially outward. A valve delivery system is introduced into the ventricle of the heart via a ventricular wall of the heart. The valve delivery system has the valve prosthesis at a distal portion thereof, wherein the valve prosthesis is in a delivery configuration. The valve delivery system is advanced through the central lumen of the radially expanded displacement component towards the annulus of the native valve of the heart. The valve prosthesis is deployed into apposition with the annulus of the native valve.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 6 is a side view of a distal portion of the chordae management catheter of FIG. 5, wherein the displacement component thereof is an inflatable balloon having a cylindrical configuration or profile and is shown in a deployed or expanded configuration.

FIG. 7 is a perspective view of the displacement component of FIG. 5, the displacement component removed from the chordae management catheter for illustrative purposes only, wherein the displacement component is an inflatable balloon having a cylindrical configuration or profile and is shown in a deployed or expanded configuration.

FIG. 8 is an end view illustration of the chordae management catheter of FIG. 5, wherein the displacement component is sealingly attached to a distal end of a shaft component so as to be longitudinally offset with the shaft component and the shaft component extends along an outermost surface of the displacement component.

FIG. 9 is an end view illustration of a chordae management catheter according to another embodiment hereof, wherein the displacement component is sealingly attached to a distal end of a shaft component so as to be longitudinally offset with the shaft component and the shaft component extends along an innermost surface of the displacement component.

FIG. 10A is a side view illustration of a distal portion of a chordae management catheter according to another embodiment hereof, a displacement component being disposed at a distalmost end of the chordae management catheter and a retractable outer sheath being utilized during delivery of the displacement component wherein the retractable outer sheath is disposed over the displacement component and the displacement component is uninflated.

FIG. 10B is a side view illustration of the distal portion of the chordae management catheter of FIG. 10A, wherein the retractable outer sheath has been retracted and the displacement component is uninflated.

FIG. 10C is a side view illustration of the distal portion of the chordae management catheter of FIG. 10A, wherein the retractable outer sheath has been retracted and the displacement component is inflated.

FIG. 10D is an end view illustration of the distal portion of the chordae management catheter of FIG. 10A, wherein the retractable outer sheath has been retracted and the displacement component is inflated.

FIG. 26 is a perspective view of a displacement component and a distal end of a chordae management catheter according to another embodiment hereof, wherein the displacement component is a planar element having a funnel configuration when deployed and wherein FIG. 26 illustrates the displacement component is its deployed configuration.

FIG. 29 is a perspective view of a displacement component according to another embodiment hereof, wherein the displacement component is a planar element having a funnel configuration when deployed with an atraumatic longitudinal outer edge and wherein FIG. 29 illustrates the displacement component is its deployed configuration.

FIG. 33 is a perspective view of a displacement component according to another embodiment hereof, wherein the displacement component is a planar element having a funnel configuration when deployed with an atraumatic circumferential distal end and wherein FIG. 33 illustrates the displacement component is its deployed configuration.

FIG. 34 is a perspective view of a displacement component according to another embodiment hereof, wherein the displacement component is a planar element having a funnel configuration when deployed with an atraumatic circumferential distal end, the displacement component including circumferential passages for receiving self-expanding filaments, and wherein FIG. 34 illustrates the displacement component is its deployed configuration.

FIG. 39 is a perspective view of a displacement component and a distal end of a chordae management catheter according to another embodiment hereof, wherein the displacement component is a planar element having a funnel configuration when deployed with an atraumatic circumferential distal end, the displacement component being deployable via rotation of a shaft of the chordae management catheter, and wherein FIG. 39 illustrates the displacement component is its deployed configuration.

DETAILED DESCRIPTION OF THE INVENTION

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or scaffold structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and polycyclooctene can be used separately or in conjunction with other shape memory polymers.

The following detailed description is merely exemplary in nature and is not intended to limit the invention or the application and uses of the invention. Although the description of embodiments hereof are in the context of delivery systems for delivering a valve prosthesis within a native mitral valve, the chordae management catheters described herein can also be used in other valves of the body that include chordae tendineae, such as for delivering a valve prosthesis within a native tricuspid valve, or for delivering a mitral or tricuspid valve prosthesis within a failed previously-implanted prosthesis. Furthermore, there is no intention to be bound by any expressed or implied theory presented in the preceding technical field, background, brief summary or the following detailed description.

Figure 1:
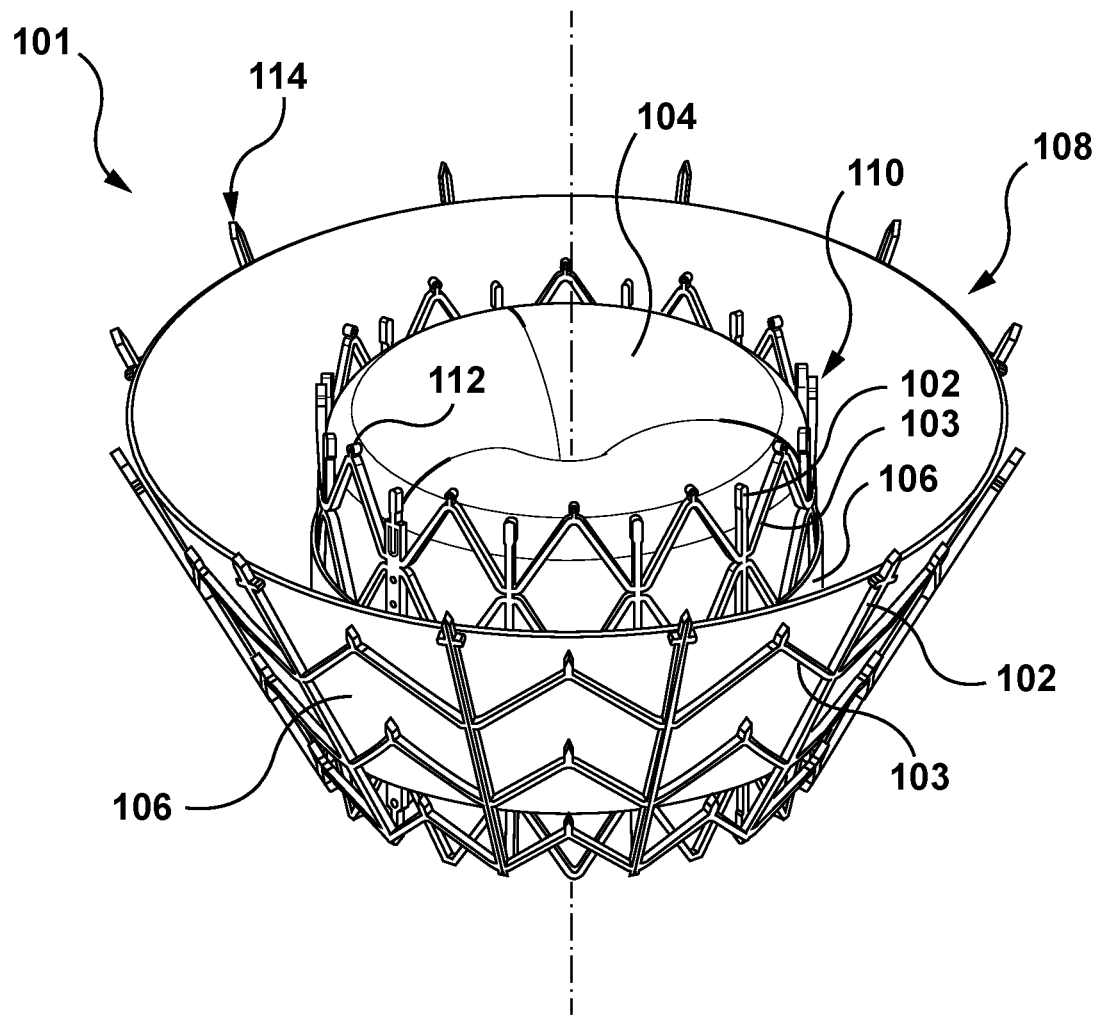
FIG. 1 is a perspective view of an exemplary transcatheter valve prosthesis for use in embodiments hereof.

Embodiments hereof are related to a valve prosthesis configured for deployment within a native heart valve of the heart in a transcatheter heart valve implantation procedure. FIG. 1 is a perspective view of an exemplary transcatheter valve prosthesis 101 for use in embodiments hereof, wherein the valve prosthesis is in an expanded, deployed configuration in accordance with an embodiment hereof. Valve prosthesis 101 is illustrated herein in order to facilitate description of the chordae management methods and devices to be utilized in conjunction with a valve delivery system according to embodiments hereof. It is understood that any number of alternate heart valve prostheses can be used with the methods and devices described herein. Valve prosthesis 101 is merely exemplary and is similar to heart valve prostheses described in more detail in U.S. Pat. No. 9,034,032 to McLean et al., which is herein incorporated by reference in its entirety. Other non-limiting examples of transcatheter valve prostheses useful with systems and methods of the present disclosure are described in U.S. Patent Application Publication Nos. 2012/0101572 to Kovalsky et al., 2012/0035722 to Tuval U.S. Pat. Appl. Pub. No. 2006/0265056 to Nguyen et al., U.S. Pat. Appl. Pub. No. 2007/05409266 to Birdsall, U.S. Pat. Appl. Pub. No. 2007/05409269 to Dolan et al., and U.S. Pat. Appl. Pub. No. 2008/00713548 to Tuval, each of which is incorporated by reference herein in its entirety and illustrate heart valve prostheses configured for placement in a mitral valve.

As shown in FIG. 1, heart valve prosthesis 101 includes a flexible anchoring member 108 at least partially surrounding and coupled to an inner valve support 110. Heart valve prosthesis 101 further includes a prosthetic valve component 104 coupled to, mounted within, or otherwise carried by valve support 110. Heart valve prosthesis 101 also includes one or more sealing members 106 and tissue engaging elements 114. For example, tissue engaging elements 114 may be spikes disposed on an upstream perimeter of anchoring member 108 and extend in an upward and/or radially outward direction to engage, and in some embodiments, penetrate the native tissue to facilitate retention or maintain position of the device in a desired implanted location. In another specific embodiment, sealing member 140 may extend around an inner wall of anchoring member 108 and/or around an exterior surface of valve support 110 to prevent paravalvular leaks between heart valve prosthesis 101 and the native tissue and/or between anchoring member 108 and valve support 110. Tissue engaging elements 114 may also be included around an outer wall of anchoring member 108 and may extend outwardly to engage and, in some embodiments, penetrate the native valve leaflets or other adjacent tissue. Additionally, valve support 110 may have a plurality of coupling features 112, such as eyelets, around an upstream end to facilitate loading, retention and deployment of heart valve prosthesis 101 within and from a delivery catheter (not shown), as further described herein.

Valve support 110 is a generally cylindrical stent or frame that supports a prosthetic valve component 104 within the interior thereof. Similarly, anchoring member 108 is also a stent or frame having a flared, funnel-like or hyperboloid shape. In some embodiments, valve support 110 and/or anchoring member 108 includes a plurality of posts 102 connected circumferentially by a plurality of struts 103. Posts 102 and struts 103 may be arranged in a variety of geometrical patterns that may expand and provide sufficient resilience and column strength for maintaining the integrity of prosthetic valve component 104. For example, posts 102 may extend longitudinally across multiple rows of struts 103 to provide column strength to the valve support 110. Generally, the plurality of posts 102 may extend along an axial direction generally parallel to the longitudinal axis and the struts 103 may extend circumferentially around and transverse to the longitudinal axis. As will be understood by one of ordinary skill in the art, the stent or frame of a valve prosthesis may have other configurations such as a metallic, polymeric, or fabric mesh or a woven construction. In embodiments hereof, valve support 110 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration as described herein. Alternatively, valve prosthesis 101 may be balloon-expandable as would be understood by one of ordinary skill in the art. Whether valve support 110 is self-expanding or balloon-expandable, valve prosthesis 101 has a compressed configuration for delivery within a valve delivery system and a radially expanded configuration for deployment within an annulus of the native valve site. In some embodiments, anchoring member 108 and/or valve support 110 may be laser cut from a single metal tube into the desired geometry, creating a tubular scaffold of interconnected struts. Anchoring member 108 may then be shaped into a desired configuration, e.g. a flared, funnel-like or hyperboloid shape, using known shape-setting techniques for such materials.

As previously mentioned, valve prosthesis 101 includes prosthetic valve component 104 within the interior of valve support 110. Prosthetic valve component 104 is configured as a one-way valve to allow blood flow in one direction and thereby regulate blood flow there-through. Prosthetic valve component 104 is capable of blocking flow in one direction to regulate flow there-through via valve leaflets that may form a bicuspid or tricuspid replacement valve. More particularly, if valve prosthesis 101 is configured for placement within a native valve having two leaflets such as the mitral valve, prosthetic valve component 104 includes two valve leaflets to form a bicuspid replacement valve that closes with pressure on the outflow and opens with pressure on the inflow. In other embodiments in accordance herewith, the prosthetic valve component may be a tricuspid replacement valve or may be a single leaflet replacement valve. The valve leaflets are sutured or otherwise securely and sealingly attached to an inner circumference of valve support 110 and/or sealing members 106 which encloses or lines valve support 110 as would be known to one of ordinary skill in the art of prosthetic tissue valve construction.

The valve leaflets may be made of pericardial material; however, the leaflets may instead be made of another material. Natural tissue for prosthetic valve leaflets for use in prosthetic valve component 104 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals, such as tissue from bovine, equine or porcine origins. Synthetic materials suitable for use as prosthetic valve leaflets in embodiments hereof include DACRON® polyester commercially available from Invista North America S.A.R.L. of Wilmington, Del., polyurethane, Gore-Tex or other cloth materials, nylon blends, polymeric materials, and vacuum deposition nitinol fabricated materials. One polymeric material from which the replacement valve leaflets may be made is an ultra-high molecular weight polyethylene material commercially available under the trade designation DYNEEMA from Royal DSM of the Netherlands. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

Sealing members 106 are formed from a suitable graft material such as a natural or biological material such as pericardium or another membranous tissue such as intestinal submucosa. Alternatively, sealing members 106 may be a low-porosity woven fabric, such as polyester, Dacron fabric, or PTFE, which creates a one-way fluid passage when attached to the stent. In one embodiment, sealing members 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Figure 2:
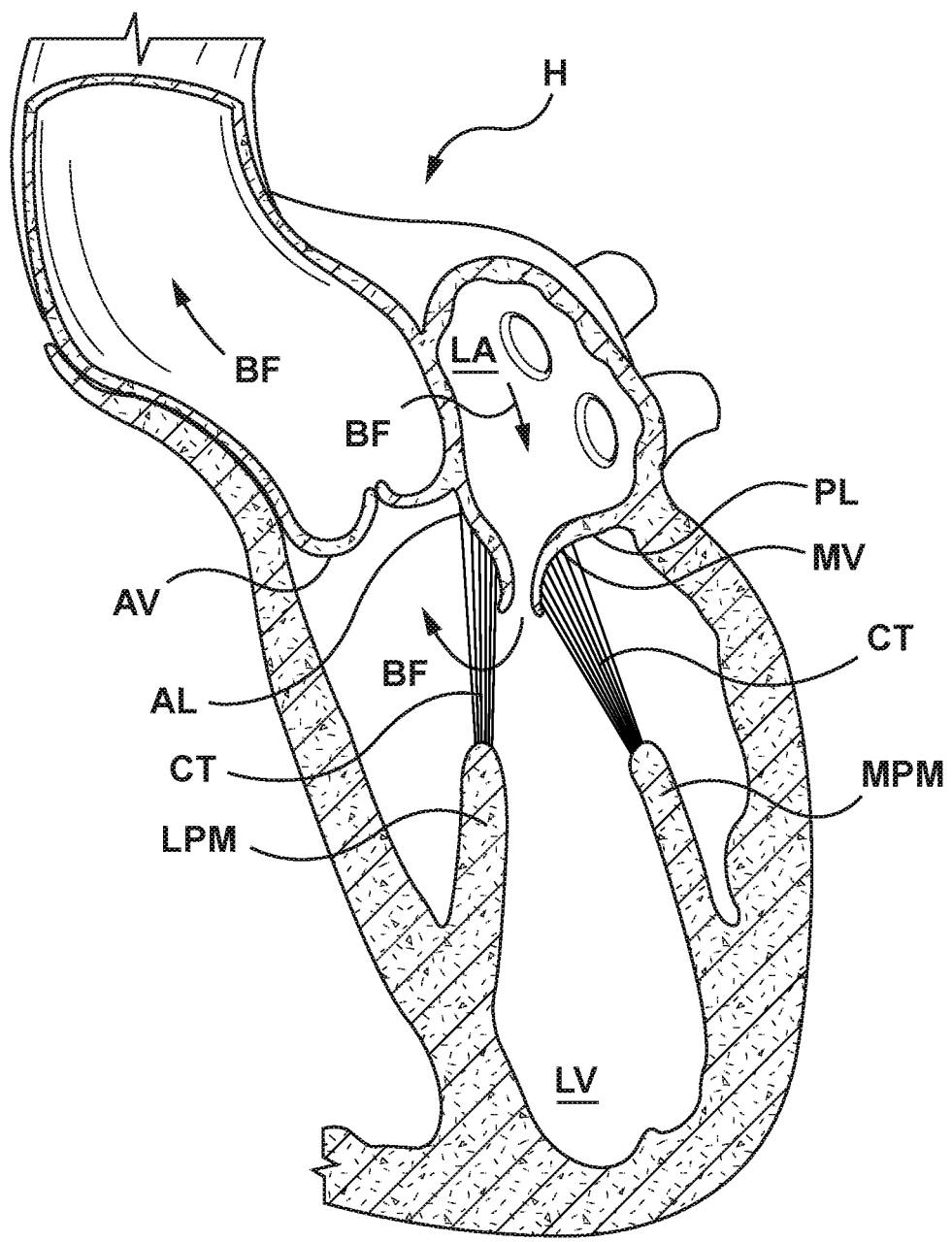
FIG. 2 is a sectional view illustration of the anatomy of a native mitral valve.

FIG. 2 illustrates a sectional view of a heart H, illustrating a left atrium LA, a left ventricle LV, a mitral valve MV and an aortic valve AV. Blood flow BF is depicted with directional arrows in FIG. 2 in the left atrium LA, into left ventricle LV through mitral valve MV, and into the aorta through aortic valve AV. Mitral valve MV is saddle-shaped and includes two native leaflets, posterior leaflet PL and anterior leaflet AL, and chordae tendineae CT extend within the left ventricle LV between the native leaflets of the mitral valve MV and the papillary muscles. As previously described herein, chordae tendineae CT are cord-like tendons that connect the medial papillary muscle MPM to the posterior leaflet PL of the mitral valve MV and connect the lateral papillary muscle LPM to the anterior leaflet AL of the mitral valve MV. When the native mitral valve is operating properly, the native leaflets will generally function in such a way that blood flows toward the left ventricle LV when the leaflets are in an open position, and so that blood is prevented from moving toward the left atrium LA when the leaflets are in a closed position. During systole, when the native leaflets close to prevent backflow of blood into the atrium, the chordae tendineae CT assist in preventing the native leaflets from everting or prolapsing into the atrium by becoming tense and holding the native leaflets in the closed position.

Figure 3:
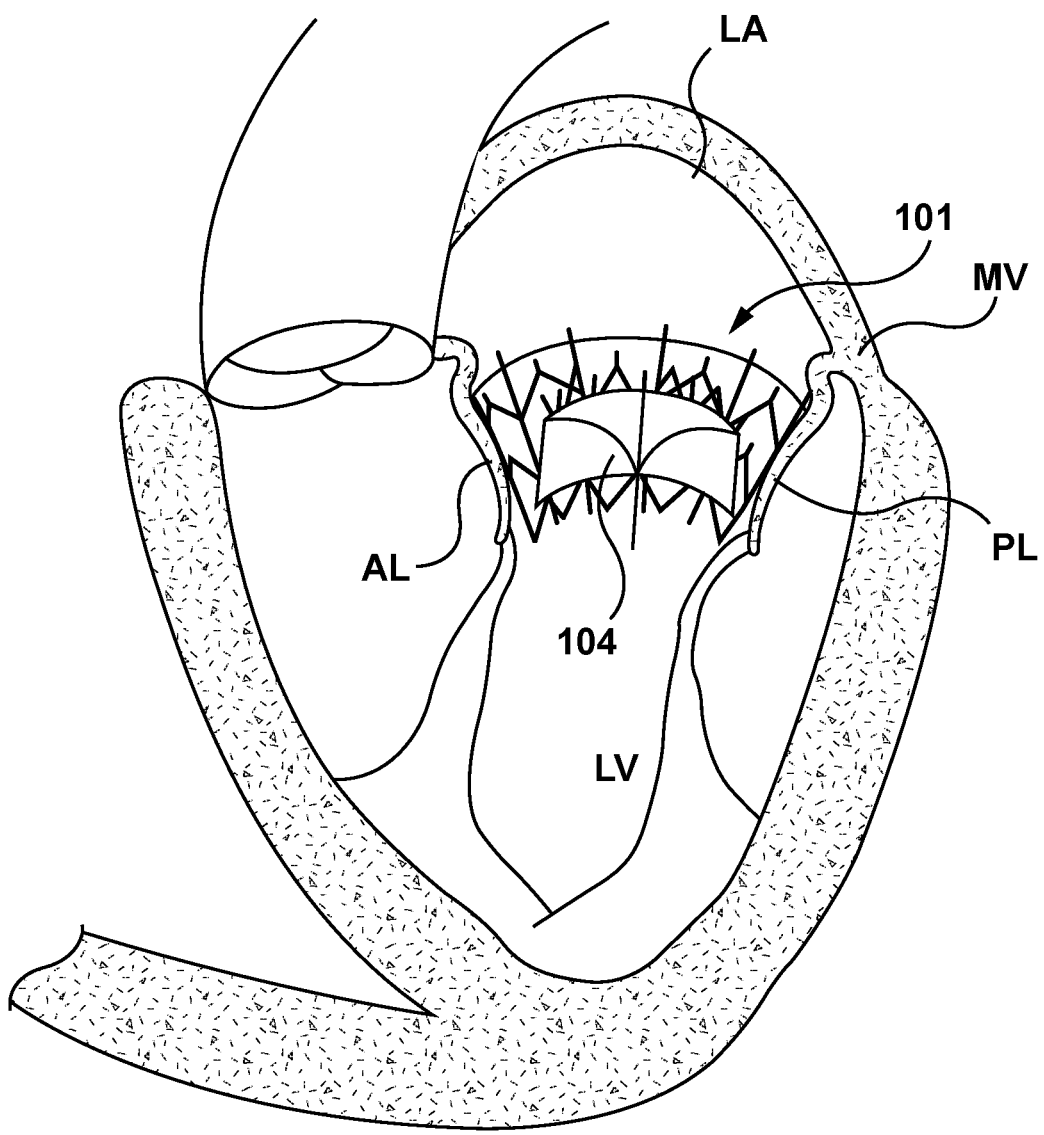
FIG. 3 is a sectional view illustration of the valve prosthesis of FIG. 1 implanted within a native mitral valve annulus.

FIG. 3 is an illustration of valve prosthesis 101 implanted within a native mitral heart valve, which is shown in section. Valve prosthesis 101 is shown deployed within a native mitral valve, with an upstream end thereof extending into the left ventricle and a downstream end thereof extending into the left atrium. When valve prosthesis 101 is deployed within the valve annulus of a native heart valve, valve support 110 and anchoring member 108 expands within native valve leaflets, posterior leaflet PL and anterior leaflet AL, of the patient's defective valve, retaining the native valve leaflets in a permanently open state.

Figure 4:
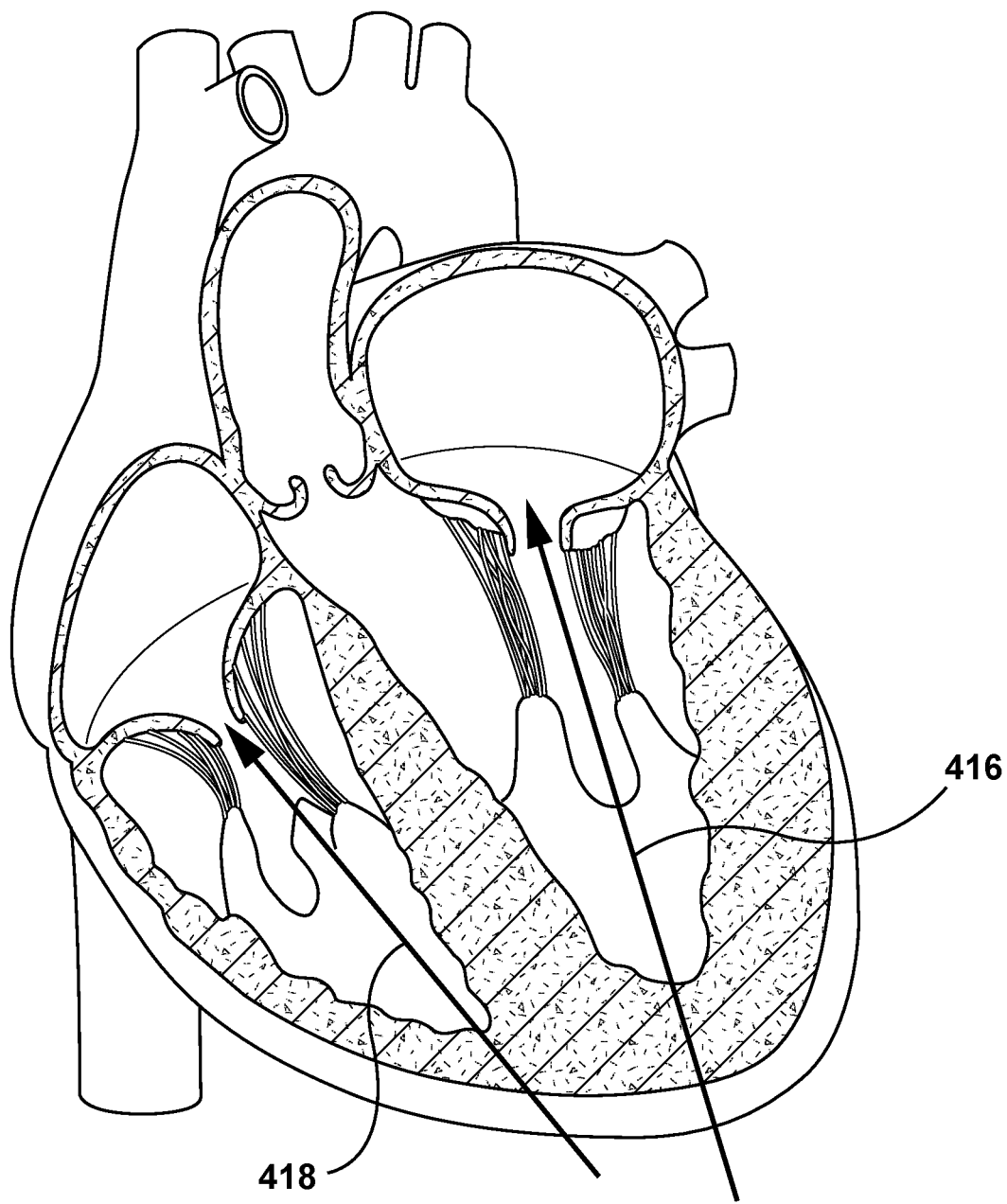
FIG. 4 is a sectional view illustration of the anatomy of heart illustrating an exemplary transapical delivery pathway or route for a transcatheter valve prosthesis.

One method of delivering valve prosthesis 101 includes delivery via a transapical approach directly through the apex of the heart via a thoracotomy, as best illustrated in FIG. 4. FIG. 4 is a sectional view illustration of the anatomy of heart illustrating an exemplary transapical delivery pathway or route represented by directional arrow 416 for delivery of valve prosthesis 101 to the native mitral valve, located between the left atrium and left ventricle. FIG. 4 also illustrates an exemplary transapical delivery pathway or route represented by directional arrow 418 for delivery of a valve prosthesis to the native tricuspid valve, located between the right atrium and right ventricle. In a transapical approach, access to the heart is gained via thoracic incision, which can be a conventional open thoracotomy or sternotomy, or a smaller intercostal or sub-xyphoid incision or puncture. An access cannula is then placed through a puncture, sealed by a purse-string suture, in the wall of the left ventricle at or near the apex of the heart. Valve delivery systems described herein may then be introduced into the left ventricle through this access cannula. The transapical approach has the feature of providing a shorter, straighter, and more direct path to the mitral or tricuspid valve. Further, because it does not involve intravascular access, the transapical procedure can be performed by surgeons who may not have the necessary training in interventional cardiology to perform the catheterizations required in other percutaneous approaches. During delivery, if self-expanding, the valve prosthesis remains compressed until it reaches a target diseased native heart valve, at which time the valve prosthesis can be released from the valve delivery system and expanded in situ via self-expansion. The valve delivery system is then removed and valve prosthesis 101 remains deployed within the native target heart valve. Alternatively, valve prosthesis 101 may be balloon-expandable and delivery thereof may be accomplished via a balloon catheter as would be understood by one of ordinary skill in the art.

However, as previously described herein, the chordae tendineae may act as an obstacle within delivery pathways 416, 418 when valve prosthesis 101 is delivered transapically and the valve delivery system may become entangled in chordae tendineae during advancement. Embodiments hereof relate to methods and devices for managing chordae tendineae during a transapical valve replacement procedure. More particularly, embodiments hereof relate to a chordae management catheter 520 having a displacement component 530 at a distal end thereof to deploy within the left or right ventricle of a heart, displacing chordae tendineae and thereby clearing a pathway for a subsequently delivered valve delivery system which is advanced through a central lumen or passageway 538 defined by displacement component 530. Displacement component 530 relocates or displaces the chordae tendineae which interfere with mitral access from the apex, while central lumen 538 defined by displacement component 530 provides a clear path or route for the valve delivery system to pass through to deploy the valve prosthesis and for the valve delivery system to be removed safely after valve deployment.

Figure 5:
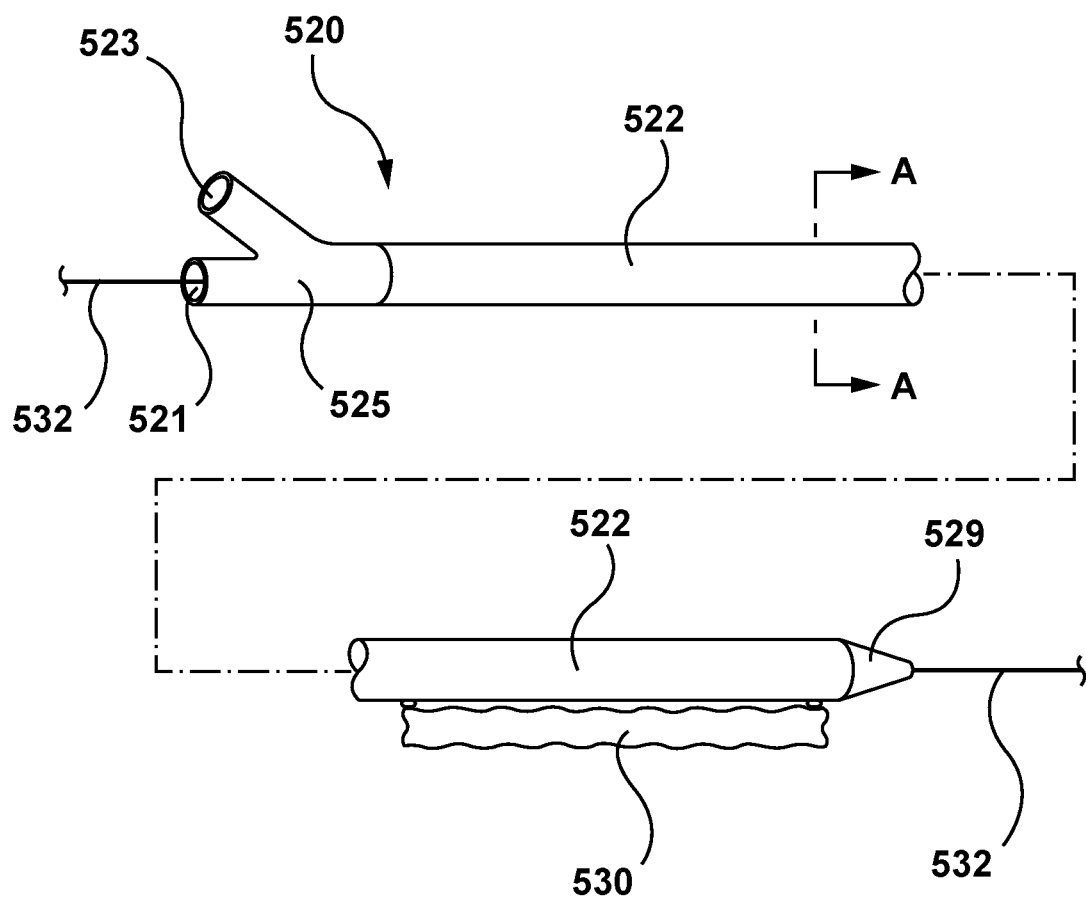
FIG. 5 is an illustration of a chordae management catheter having a displacement component or balloon at a distal end thereof according to an embodiment hereof, wherein the displacement component is in a delivery or unexpanded configuration.
Figure 5A:
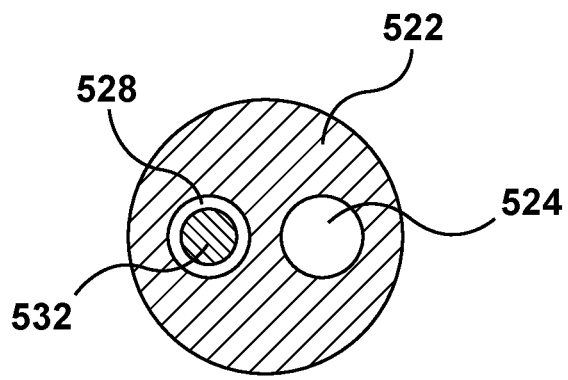
FIG. 5A is a cross-sectional view taken along line A-A of FIG. 5.

Chordae management catheter 520 will be described in more detail with reference to FIG. 5 and FIG. 5A which is a cross-sectional view taken along line A-A of FIG. 5. FIG. 5 is a side view of chordae management catheter 520 with displacement component 530 is in a delivery or unexpanded configuration. FIGS. 6 and 7 depict side and perspective views, respectively, of displacement component 530 in a radially expanded or inflated configuration. In the embodiment of FIG. 5, displacement component 530 is an inflatable balloon. In the expanded or inflated configuration, displacement component 530 is a cylindrical inflatable balloon that defines a central lumen or passageway 538 therethrough. U.S. Pat. No. 4,909,252 to Goldberger, incorporated by reference herein in its entirety, describes an annular or ring-shaped balloon that may be modified for use in embodiments hereof. Expanded displacement component 530 has an annular cross-section with an outer wall or circumferential surface 534 and an inner wall or circumferential surface 536 with an interior space or volume 535 being defined between outer and inner walls 534, 536. Depending upon the size of the patient, outer wall 534 may diametrically vary from 20-60 mm depending upon patient anatomy and inner wall 536 can diametrically vary from 8-45 mm depending on the delivery device used therewith. In an embodiment, outer wall 534 may be approximately 20 mm and inner wall 536 may be approximately 14 mm. Central lumen 538 allows for subsequent delivery of a valve delivery system and thus inner wall 536 is sized to be slightly greater than the outer profile of the valve delivery system in order to provide clearance therebetween. More particularly, central lumen 538 is sized and configured to allow a valve delivery system to be subsequently delivered through expanded displacement component 530 in order to guide the valve delivery system to the native valve annulus prior to deployment of the valve prosthesis contained within the valve delivery system. Expanded displacement component 530 is positioned within the native valve annulus at the beginning of a valve replacement/repair procedure in order to push or displace chordae tendineae and clear a pathway or route for a later-introduced valve delivery system within the left or right ventricle for a more successful prosthetic valve deployment.

Chordae management catheter 520 includes a shaft component 522, a luer hub 525 disposed at a proximal end of shaft component 522, and a tapered distal tip 529 disposed at a distal end of shaft component 522. As would be understood by one of ordinary skill in the art of balloon catheter design, the proximal portion of chordae management catheter 520 extends outside of a patient and includes luer hub 525 or other type of fitting having a proximal guidewire port 521 and a proximal inflation port 523 that may be connected to a source of inflation fluid. Shaft component 522 is formed by multi-lumen profile extrusion and defines a guidewire lumen 528 therethrough and an inflation lumen 524 which is in fluid communication with interior space or volume 535 of displacement component 530. Guidewire lumen 528 is sized to slidingly receive guidewire 532 through proximal guidewire port 532 of luer hub 525 such that chordae management catheter 520 is configured to be tracked over the guidewire during delivery thereof as shown in FIG. 5.

At least a portion of displacement component 530 is sealingly attached to shaft component 522 so as to be longitudinally offset from shaft component 522. In the embodiment of FIG. 5, displacement component 530 is sealingly attached to an outer surface of shaft component 522 at attachment points 526A, 526B positioned at proximal and distal ends of displacement component 530. Along at least one of attachment points 526A, 526B, shaft component 522 includes a distal inflation port or opening (not shown) to provide fluid communication between inflation lumen 524 and interior volume 535 of displacement component 530. Inflation lumen 524 allows inflation fluid received through a luer hub 525 at a proximal end of chordae management catheter 520 to be delivered to displacement component 530. When inflation fluid is provided within inflation lumen 524, it fills interior volume 535 of displacement component 530 in order to inflate the displacement component into the expanded configuration. In an embodiment hereof, the inflation fluid to inflate displacement component 530 includes a contrast agent so that expanded displacement component 530 provides constant visualization thereof during the valve replacement/repair procedure.

Shaft component 522 is formed of any suitable flexible polymeric material. Non-exhaustive examples of material for the shaft component are polyethylene terephalate (PET), nylon, polyethylene, PEBAX, or combinations of any of these, either blended or co-extruded. Optionally, a portion of the shaft component is formed as a composite having a reinforcement material incorporated within a polymeric body to enhance strength, flexibility, and/or toughness. Suitable reinforcement layers include braiding, wire mesh layers, embedded axial wires, embedded helical or circumferential wires, and the like. In an embodiment, a proximal portion of shaft component 522 may in some instances be formed from a metallic tubing, such as a hypotube, or a reinforced polymeric tube as shown and described, for example, in U.S. Pat. No. 5,827,242 to Follmer et al., which is incorporated by reference herein in its entirety. Shaft component 522 may have any suitable working length to extend to a target location within the body vessel.

Displacement component 530 may be made of a polymeric material such as may commonly be used for dilatation balloons, including without limitation polyethylene terephthalate (PET), polyamide 12 or polyethylene block amide copolymer. In an embodiment hereof, a coating is applied to inner wall or circumferential surface 536 of displacement component 530 such that the inner wall is stronger than outer wall or circumferential surface 534 of displacement component 530. In an embodiment, the coating may be an abrasion and puncture-resistant coating such as but limited to a thermoplastic or thermosetting polymeric material. In another embodiment, inner wall or circumferential surface 536 of displacement component 530 may be formed from a second stronger than outer wall or circumferential surface 534 of displacement component 530 in a dual layer configuration that may be formed via co-extrusion. Inner wall or circumferential surface 536 of displacement component 530 may contact the valve delivery system when the valve delivery system is passed through central lumen 538, and thus applying a coating thereto may make it stronger to resist tearing during advancement of the valve delivery system.

Other types of catheter construction are also amendable to the invention, such as, without limitation thereto, a coaxial catheter construction including coaxial inner and outer shafts with an annular inflation lumen defined between an inner surface of the outer shaft and an outer surface of inner shaft. In the embodiment of FIG. 5, chordae management catheter 520 has an over-the-wire (OTW) catheter configuration with guidewire lumen 528 extending substantially the entire length of the catheter for accommodating a guidewire. In another embodiment (not shown), chordae management catheter 520 is modified to be of a rapid exchange (RX) catheter configuration without departing from the scope of the present invention such that guidewire lumen 528 extends within only the distal portion of chordae management catheter 520.

In addition, displacement component 530 may be sealing attached to shaft component 522 in any suitable manner so long as inflation lumen 524 is in fluid communication with interior space or volume 535 of displacement component 530. More particularly, as best shown in FIG. 8, displacement component 530 is sealingly attached to a distal end of shaft component 522 so that shaft component 522 extends along an outermost surface of displacement component 530. In another embodiment shown in FIG. 9, a displacement component 930 is sealingly attached to a distal end of a shaft component 922 so that shaft component 922 extends along an innermost surface of displacement component 930 within a central lumen 938 of displacement component 930. By disposing shaft component 922 within central lumen 928 of displacement component 930, displacement component 930 may be configured to radially expand to a relatively wider dimension that essentially fills the left or right ventricle.

In another embodiment shown in FIGS. 10A-10D, a chordae management catheter 1020 includes a retractable outer sheath 1027 disposed over a shaft component 1022. Displacement component 1030 is an inflatable balloon similar to displacement component 530, but in this embodiment displacement component 1030 is attached a distalmost end or tip of shaft component 1022. Shaft component 1022 defines an inflation lumen (not shown) therethrough which is in fluid communication with an interior space or volume of displacement component 1030 and may also define a guidewire lumen (not shown). Outer sheath 1027 is provided to contain displacement component 1030 during delivery as shown in FIG. 10A, and is retracted when it is desired to inflate displacement component 1030 as shown in FIGS. 10B-10D. More particularly, FIG. 10B illustrates outer sheath 1027 retracted but displacement component 1030 not yet inflated while FIGS. 10C and 10D are side and end views, respectively, after inflation of displacement component 1030. Due to the disposition of displacement component 1030 at a distalmost end or tip of shaft component 1022, chordae management catheter 1020 may particularly be useful when positioned into the left ventricle via a transaortic approach as described in FIGS. 23 and 24 because central lumen 1038 of displacement component 1030 is disposed distal to chordae management catheter 1020 when displacement component 1030 is inflated.

Figure 11:
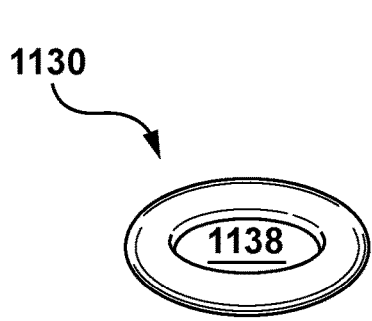
FIG. 11 is a perspective view of a displacement component according to another embodiment hereof, wherein the displacement component is an inflatable balloon having an annular configuration or profile and is shown in a deployed or expanded configuration.
Figure 12:
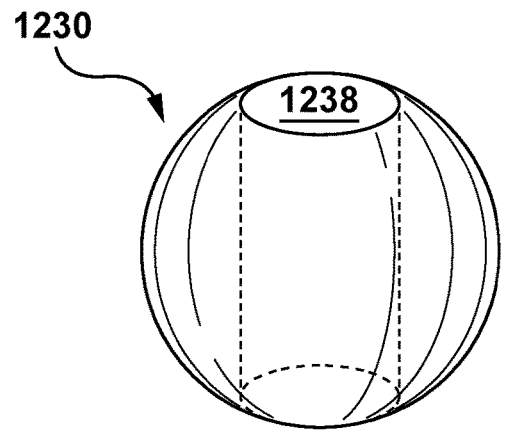
FIG. 12 is a perspective view of a displacement component according to another embodiment hereof, wherein the displacement component is an inflatable balloon having spherical configuration or profile and is shown in a deployed or expanded configuration.
Figure 13:
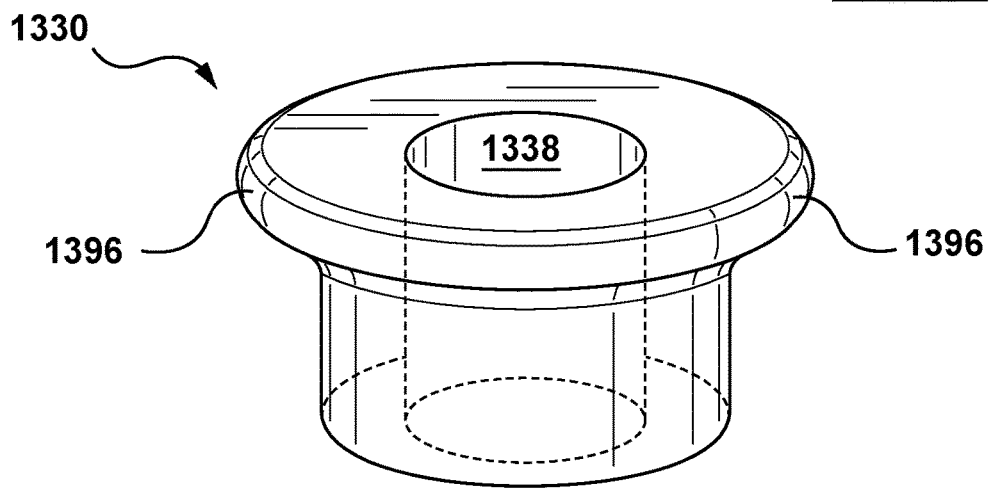
FIG. 13 is a perspective view of a displacement component according to another embodiment hereof, wherein the displacement component is an inflatable balloon having cylindrical configuration or profile with a distalmost flange or brim and is shown in a deployed or expanded configuration.

Although depicted with a cylindrical inflated profile or configuration, the displacement component 530 may have other configurations that are configured to push or displace chordae tendineae and clear a pathway or route for a later-introduced valve delivery system within the left or right ventricle. For example, FIG. 11 is a perspective view of a displacement component 1130 shown in a deployed or expanded configuration according to another embodiment hereof. In the expanded or inflated configuration, displacement component 1130 is an annular component having a donut-shaped or toroid-shaped configuration such that the cross-section thereof defines a central opening or lumen 1138 therethrough. FIG. 12 is a perspective view of a displacement component 1230 shown in a deployed or expanded configuration according to another embodiment hereof. In the expanded or inflated configuration, displacement component 1230 has a spherical inflated profile or configuration rather than cylindrical. Displacement component 1230 defines a central opening or lumen 1238 therethrough for subsequent delivery of a valve delivery system. FIG. 13 is a perspective view of a displacement component 1330 shown in a deployed or expanded configuration according to another embodiment hereof. In the expanded or inflated configuration, displacement component 1230 has a cylindrical profile or configuration but also includes a distalmost flange or brim 1396 having an outer diameter greater than the outer diameter of the remaining length of the displacement component. Displacement component 1330 defines a central opening or lumen 1338 therethrough for subsequent delivery of a valve delivery system. When inflated in situ, distalmost flange or brim 1396 is configured to be disposed within the left atrium and contact the annulus of the native mitral valve to anchor displacement component 1330 during delivery of the valve delivery system. In an embodiment hereof, distalmost flange or brim 1396 may be formed from a radiopaque material and/or include a radiopaque coating to act as a radiopaque marker during valve implantation.

Figure 14:
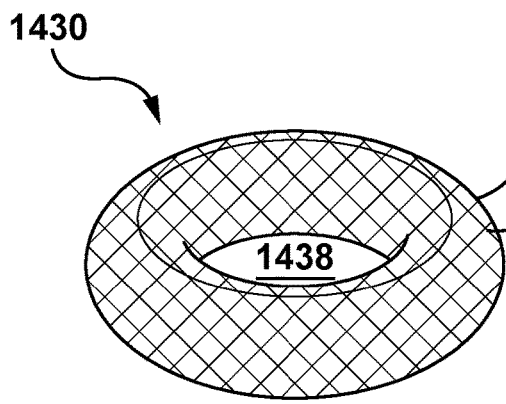
FIG. 14 is a perspective view of a displacement component according to another embodiment hereof, wherein the displacement component is an expandable mesh having an annular configuration or profile and is shown in a deployed or expanded configuration.
Figure 15:
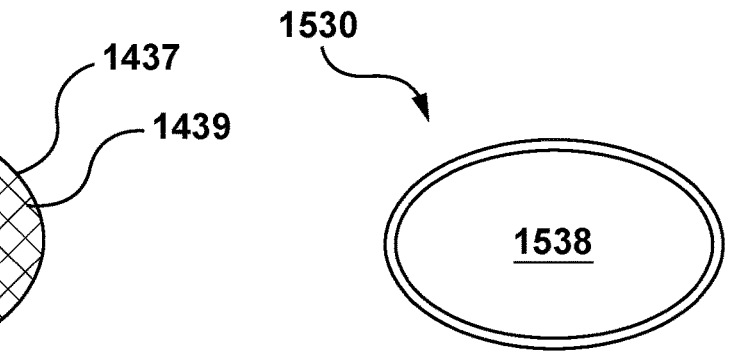
FIG. 15 is a perspective view of a displacement component according to another embodiment hereof, wherein the displacement component is an expandable ring and is shown in a deployed or expanded configuration.

FIG. 14 is a perspective view of a displacement component 1430 according to another embodiment hereof. Displacement component 1430 is an expandable mesh or braid component having an annular configuration or profile and is shown in a deployed or expanded configuration. Displacement component 1430 includes a braided structure constructed from a plurality of metallic wires or filaments woven together or a stamped mesh 1437 that has a toroid-shaped -shaped or donut-shaped configuration such that a cross-section thereof defines a central opening or lumen 1438 therethrough to allow for subsequent delivery of a valve delivery system. Open spaces 1439 defined by mesh 1437 when displacement component 1430 is expanded allow blood or other fluid to flow therethrough during the valve replacement/repair procedure such that the blood flow is not blocked or occluded. In an embodiment shown in FIG. 14, displacement component 1430 is self-expanding meaning it has a mechanical memory to return to the expanded or deployed configuration. Mechanical memory may be imparted to the braided wire or mesh structure that forms displacement component 1430 by thermal treatment to achieve a spring temper in stainless steel, for example, or to set a shape memory in a susceptible metal alloy, such as nitinol. Expandable displacement component 1430 is held or compressed in its delivery configuration within an outer sheath (not shown) so that displacement component 1430 is configured to be tracked through the vasculature in a low profile. When it is desired to expand displacement component 1430 into the annular toroid-shaped -shaped or donut-shaped configuration, the outer sheath is withdrawn such that displacement component 1430 is released and allowed to assume its expanded configuration. In another embodiment hereof depicted in FIG. 15, a displacement component 1530 may be an expandable ring that defines opening or lumen 1538 therethrough and is formed from a self-expanding material so that it operates similar to displacement component 1430.

Figure 44:
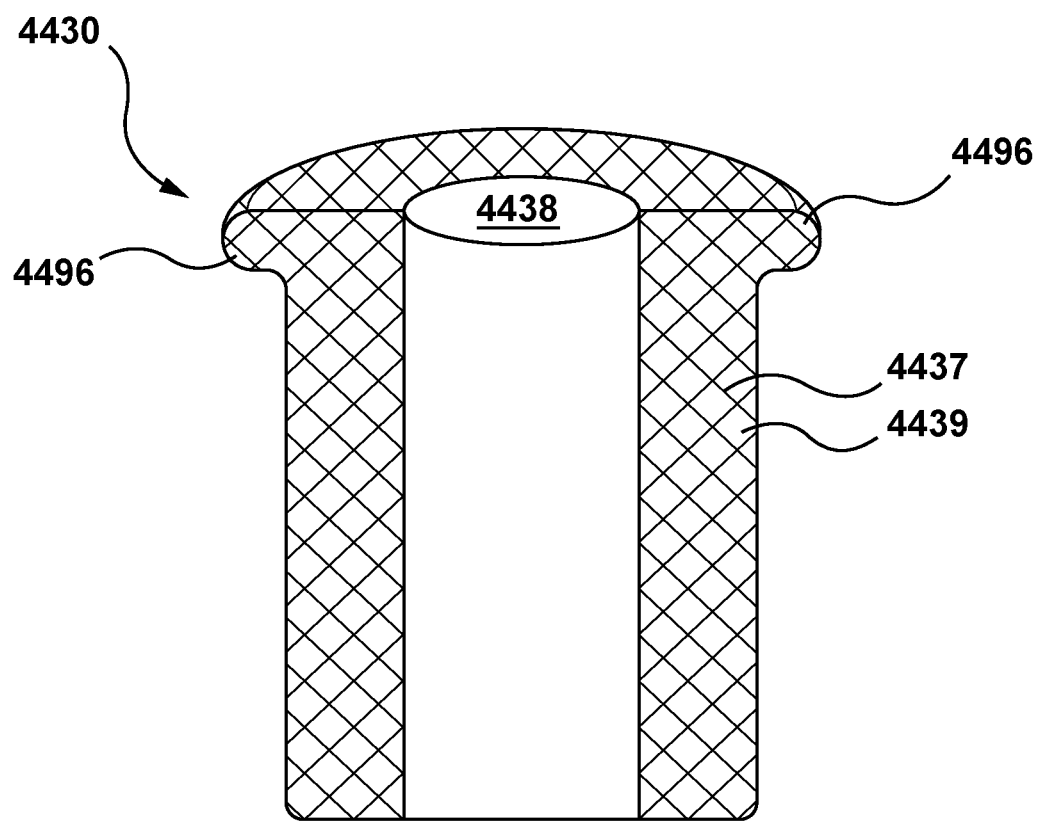
FIG. 44 is a perspective view of a displacement component according to another embodiment hereof, wherein the displacement component is an expandable mesh having cylindrical configuration or profile with a distalmost flange or brim and is shown in a deployed or expanded configuration, and wherein the displacement component is configured to release from the chordae management catheter and anchor within the left atrium to subsequently become part of the heart valve prosthesis after implantation thereof to prevent paravalvular leakage.

In an embodiment hereof, the displacement component may be configured to release from the chordae management catheter and anchor within the left atrium to subsequently become part of the heart valve prosthesis after implantation thereof to prevent paravalvular leakage. More particularly, FIG. 44 is a perspective view of a displacement component 4430 shown in a deployed or expanded configuration according to another embodiment hereof. Displacement component 4430 is an expandable mesh or braid component that defines a central opening or lumen 4438 therethrough to allow for subsequent delivery of a valve delivery system. Displacement component 4430 includes a braided structure constructed from a plurality of metallic wires or filaments woven together or a stamped mesh 4437. Open spaces 4439 defined by mesh 4437 when displacement component 4430 is expanded allow blood or other fluid to flow therethrough during the valve replacement/repair procedure such that the blood flow is not blocked or occluded. In the expanded or deployed configuration, displacement component 4430 has a cylindrical profile or configuration but also includes a distalmost flange or brim 4496 having an outer diameter greater than the outer diameter of the remaining length of the displacement component. When deployed in situ, distalmost flange or brim 4496 is configured to be disposed within the left atrium and contact the annulus of the native mitral valve to anchor displacement component 4430 during delivery of the valve delivery system. In an embodiment hereof, distalmost flange or brim 4496 may be formed from a radiopaque material and/or include a radiopaque coating to act as a radiopaque marker during valve implantation. Displacement component 4430 is self-expanding meaning it has a mechanical memory to return to the expanded or deployed configuration. Mechanical memory may be imparted to the braided wire or mesh structure that forms displacement component 4430 by thermal treatment to achieve a spring temper in stainless steel, for example, or to set a shape memory in a susceptible metal alloy, such as nitinol. Expandable displacement component 4430 is held or compressed in its delivery configuration within an outer sheath (not shown) so that displacement component 4430 is configured to be tracked through the vasculature in a low profile. When it is desired to expand displacement component 4430 into the deployed configuration, the outer sheath is withdrawn such that displacement component 4430 is released from the chordae management catheter and allowed to assume its expanded configuration.

Displacement component 4430 is formed from a relatively soft or semi-soft material such as a self-expanding polymeric material. Once it is delivered and deployed within the native valve, distalmost flange or brim 4496 is disposed within the left atrium and contacts the annulus of the native mitral valve to anchor displacement component 4430, thereby permitting removal of the chordae management catheter. Central opening or lumen 4438, as well as open spaces 4439 defined by mesh 4437, allow blood or other fluid to flow therethrough during delivery of the valve prosthesis such that the blood flow is not blocked or occluded. The valve delivery catheter may then be advanced through central opening or lumen 4438, and the valve prosthesis may be deployed within central opening or lumen 4438. When the valve prosthesis is deployed within displacement component 4430, the radial force of the valve prosthesis fixes or secures the valve prosthesis and displacement component 4430 together. More particularly, since displacement component 4430 is formed from a relatively soft or semi-soft material, expansion of the valve prosthesis compresses displacement component 4430 and thereby secures displacement component 4430 between the expanded valve prosthesis and the native anatomy. Once sandwiched between the expanded valve prosthesis and the native anatomy, displacement component 4430 substantially fills any/all gaps or cavities/crevices between the outer surface of the expanded valve prosthesis and native valve tissue that may be caused due the valve prosthesis not conforming to the native anatomy due to stenosis, calcium or irregular leaflet formation. "Substantially" as utilized herein means that blood flow through the target gap or cavity is occluded or blocked, or stated another way blood is not permitted to flow there through. Once sandwiched between the expanded valve prosthesis and the native anatomy, displacement component 4430 functions as a continuous circumferential seal around the heart valve prosthesis to block or prevent blood flow around the outer perimeter of the valve prosthesis, thereby minimizing and/or eliminating any paravalvular leakage at the implantation site.

Figure 45:
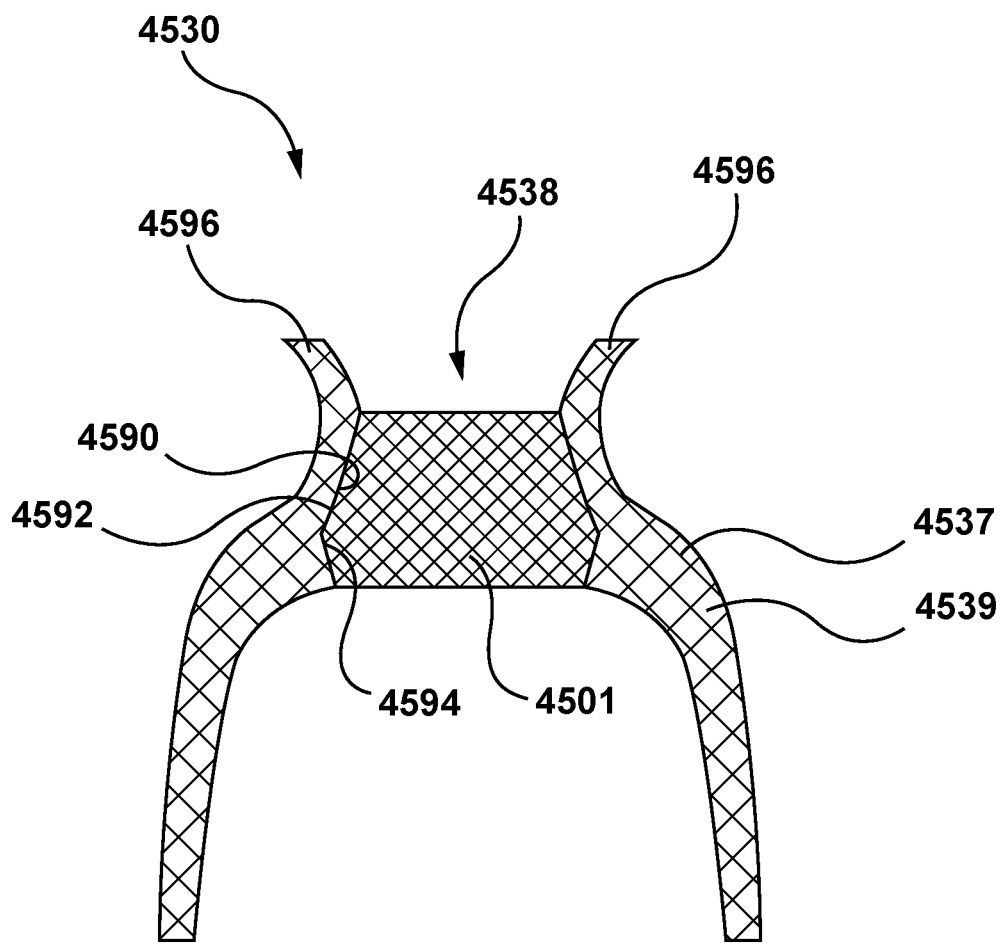
FIG. 45 is a side view of a displacement component and a valve prosthesis deployed therein according to another embodiment hereof, wherein the displacement component is similar to the displacement component of FIG. 44 except that the expanded valve prosthesis and the displacement component include irregular, mating surfaces in order to create a perfect fit between the components when expanded in situ.

In order to improve securement between the expanded valve prosthesis and displacement component 4430, the expanded valve prosthesis and displacement component 4430 may include irregular, mating surfaces in order to create a perfect fit between the components when expanded in situ. For example, as shown in FIG. 45, an inner surface 4590 of a displacement component 4530 includes a female notch 4592 formed thereon. Stated another way, central opening or lumen 4538 includes female notch 4592 formed thereon. Displacement component 4530 is similar to displacement component 4530 and includes an expandable mesh or braid component that defines a central opening or lumen 4538 therethrough to allow for subsequent delivery of a valve delivery system. Open spaces 4539 defined by mesh 4537 when displacement component 4530 is expanded allow blood or other fluid to flow therethrough during the valve replacement/repair procedure such that the blood flow is not blocked or occluded. In the expanded or deployed configuration, displacement component 4530 has a cylindrical profile or configuration but also includes a distalmost flange or brim 4596 having an outer diameter greater than the outer diameter of the remaining length of the displacement component which is configured to be disposed within the left atrium and contact the annulus of the native mitral valve to anchor displacement component 4530 during delivery of the valve delivery system. Displacement component 4530 is formed from a relatively soft or semi-soft material such as a self-expanding polymeric material. When a valve prosthesis 4501 is deployed within displacement component 4530, the radial force of the valve prosthesis fixes or secures the valve prosthesis and displacement component 4530 together. Once sandwiched between expanded valve prosthesis 4501 and the native anatomy, displacement component 4530 substantially fills any/all gaps or cavities/crevices between the outer surface of the expanded valve prosthesis and native valve tissue that may be caused due the valve prosthesis not conforming to the native anatomy due to stenosis, calcium or irregular leaflet formation. Valve prosthesis 4501 may be similar to valve prosthesis 101 described above except that it is modified to include a male projection 4594 that is configured to mate with female notch 4592. When valve prosthesis 4501 is expanded within central opening or lumen 4538, male projection 4594 of valve prosthesis 4501 fits securely within female notch 4592 of displacement component 4530 to enhance the fit between the components.

Figure 16:
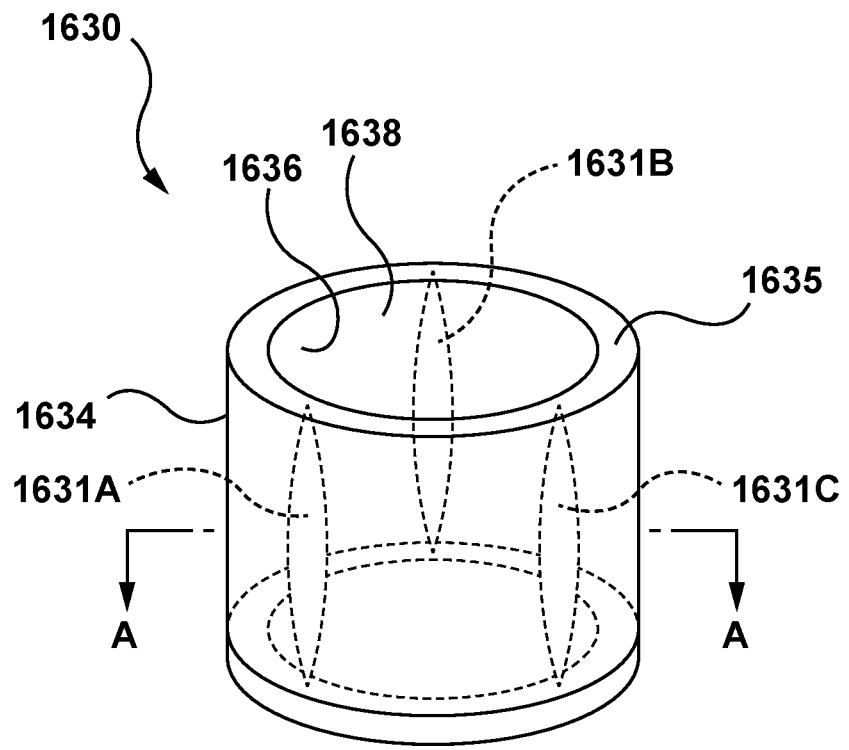
FIG. 16 is a perspective view of a displacement component according to another embodiment hereof, wherein the displacement component is an inflatable balloon having a cylindrical configuration or profile and is shown in a deployed or expanded configuration, the cylindrical balloon including integral channels for receiving contrast solution.
Figure 16A:
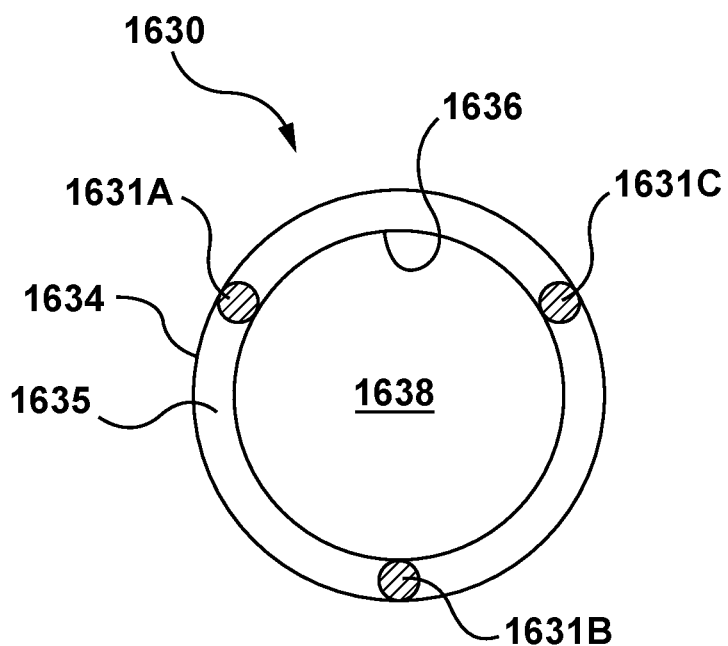
FIG. 16A is a cross-sectional view taken along line A-A of FIG. 16.

FIG. 16 is a perspective view of a displacement component 1630 according to another embodiment hereof, while FIG. 16A is a cross-sectional view of displacement component 1630 taken along line A-A of FIG. 16. In the expanded or inflated configuration shown in FIGS. 16 and 16A, displacement component 1630 is a cylindrical inflatable balloon that defines central lumen or passageway 1638 therethrough. Similar to central lumen 538, central lumen 1638 allows for subsequent delivery of a valve delivery system. More particularly, central lumen 1638 is sized and configured to allow a valve delivery system to be subsequently delivered through expanded displacement component 1630 in order to guide the valve delivery system to the native valve annulus prior to deployment of the valve prosthesis contained within the valve delivery system. Expanded displacement component 1630 is positioned within the native valve annulus at the beginning of a valve replacement/repair procedure in order to push or displace chordae tendineae and clear a pathway or route for a later-introduced valve delivery system within the left or right ventricle for a more successful prosthetic valve deployment. Expanded displacement component 1630 has an annular cross-section with an outer wall or circumferential surface 1634 and an inner wall or circumferential surface 1636 with an interior space or volume 1635 being defined between outer and inner walls 1634, 1636.

Displacement component 1630 includes a plurality of integral channels or pockets 1631A, 1631B, 1631C (collectively referred to herein as pockets 1631) within interior space or volume 1635 for receiving contrast solution. Integral pockets 1631 provide markers to assist in properly aligning and positioning the valve delivery system which is subsequently delivered through central lumen 1638 of expanded displacement component 1630. Pockets 1631 form a pattern or geometry to make displacement component 1630 more visible under fluoroscopy than a balloon without the pattern. In an embodiment, as shown in FIG. 16, the pattern or geometry includes three circumferentially spaced apart pockets 1631 although other patterns may be suitable.

Figure 17:
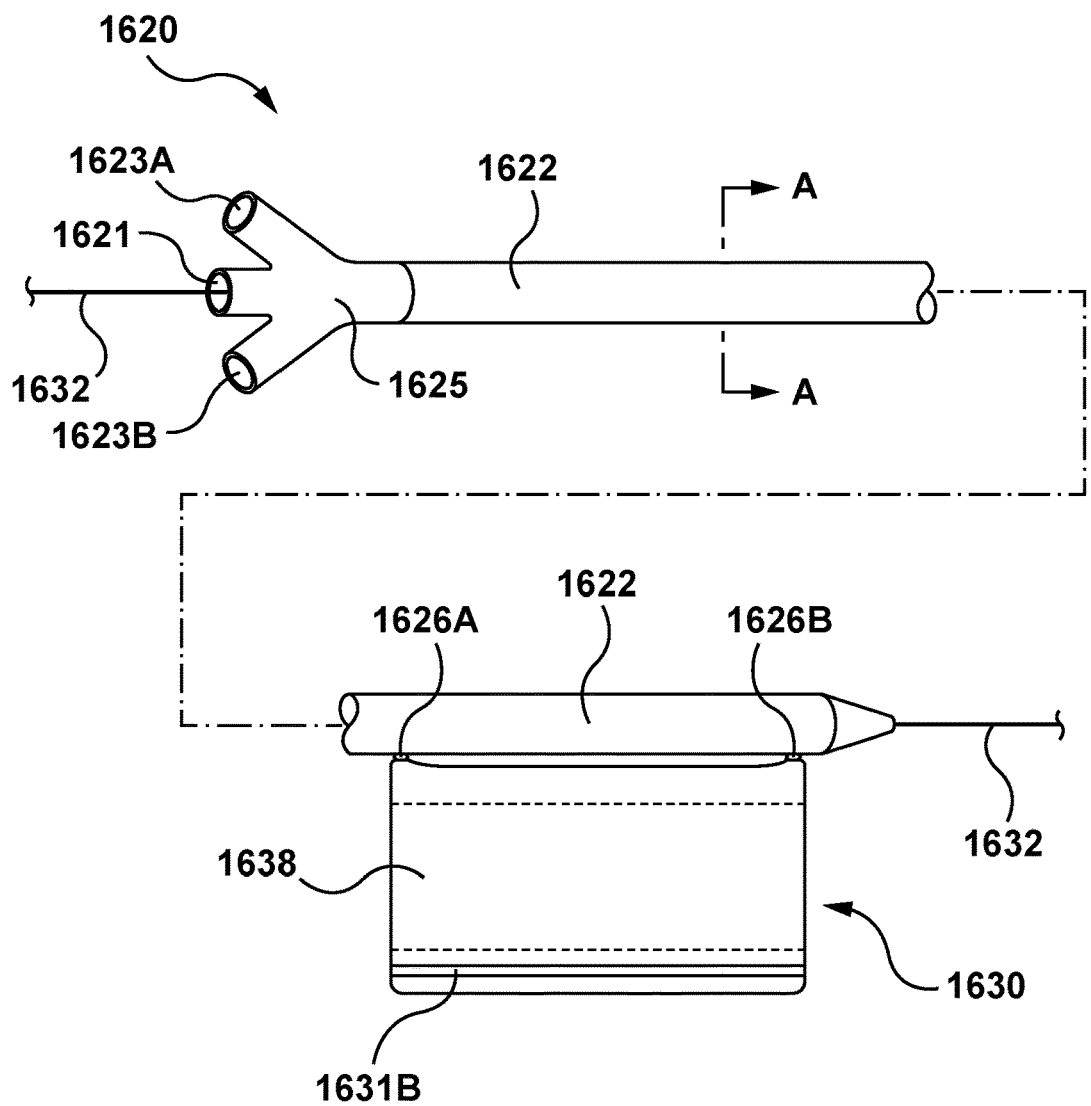
FIG. 17 is a perspective illustration of a chordae management catheter having the displacement component of FIG. 16 attached thereto, wherein the displacement component is in an expanded or inflated configuration.
Figure 17A:
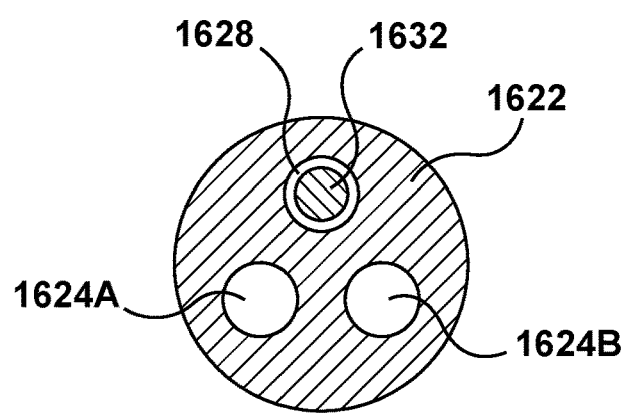
FIG. 17A is a cross-sectional view taken along line A-A of FIG. 17.

FIG. 17 is a perspective illustration of a chordae management catheter 1620 having displacement component 1630 attached thereto. FIG. 17A is a cross-sectional view taken along line A-A of FIG. 17. As opposed to a single inflation lumen, chordae management catheter 1620 includes a first inflation lumen 1624A for delivering a contrast solution and a second inflation lumen 1624B for delivering saline solution. More particularly, chordae management catheter 1620 includes a shaft component 1622 and a luer hub 1625 disposed at a proximal end of shaft component 1622, with luer hub 1626 having a proximal guidewire port 1621 and two proximal inflation ports 1623A, 1623B that may be connected to a source of inflation fluid. Shaft component 1622 is formed by multi-lumen profile extrusion and defines a guidewire lumen 1628 therethrough as well as first and second inflation lumens 1624A, 1624B. Guidewire lumen 1628 is sized to slidingly receive guidewire 1632 through proximal guidewire port 1632 of luer hub 1625 such that chordae management catheter 1620 is configured to be tracked over the guidewire during delivery thereof as shown in FIG. 17.

At least a portion of displacement component 1630 is sealingly attached to shaft component 1622 so as to be longitudinally offset with shaft component 1622. In the embodiment of FIG. 16, displacement component 1630 is sealingly attached to an outer surface of shaft component 1622 at attachment points 1626A, 1626B positioned at proximal and distal ends of displacement component 1630. Along attachment point 526A, shaft component 1622 includes a first distal inflation port or opening (not shown) to provide fluid communication between first inflation lumen 1624A and the interior volume of pockets 1631 of displacement component 530. Inflation lumen 1624A allows contrast solution received through proximal inflation port 1623A of luer hub 1625 at a proximal end of chordae management catheter 1620 to be delivered to displacement component 1630. When contrast solution is provided within first inflation lumen 1624A, it fills the interior volume of pockets 1631 of displacement component 530. Along attachment point 526B, shaft component 1622 includes a second distal inflation port or opening (not shown) to provide fluid communication between second inflation lumen 524B and interior volume 1635 of displacement component 1630. Inflation lumen 1624B allows inflation fluid received through proximal inflation port 1623B of luer hub 1625 at a proximal end of chordae management catheter 1620 to be delivered to displacement component 1630. When inflation fluid is provided within inflation lumen 1624B, it fills interior volume 1635 of displacement component 1630 in order to inflate the displacement component into the expanded configuration.

Figure 18:
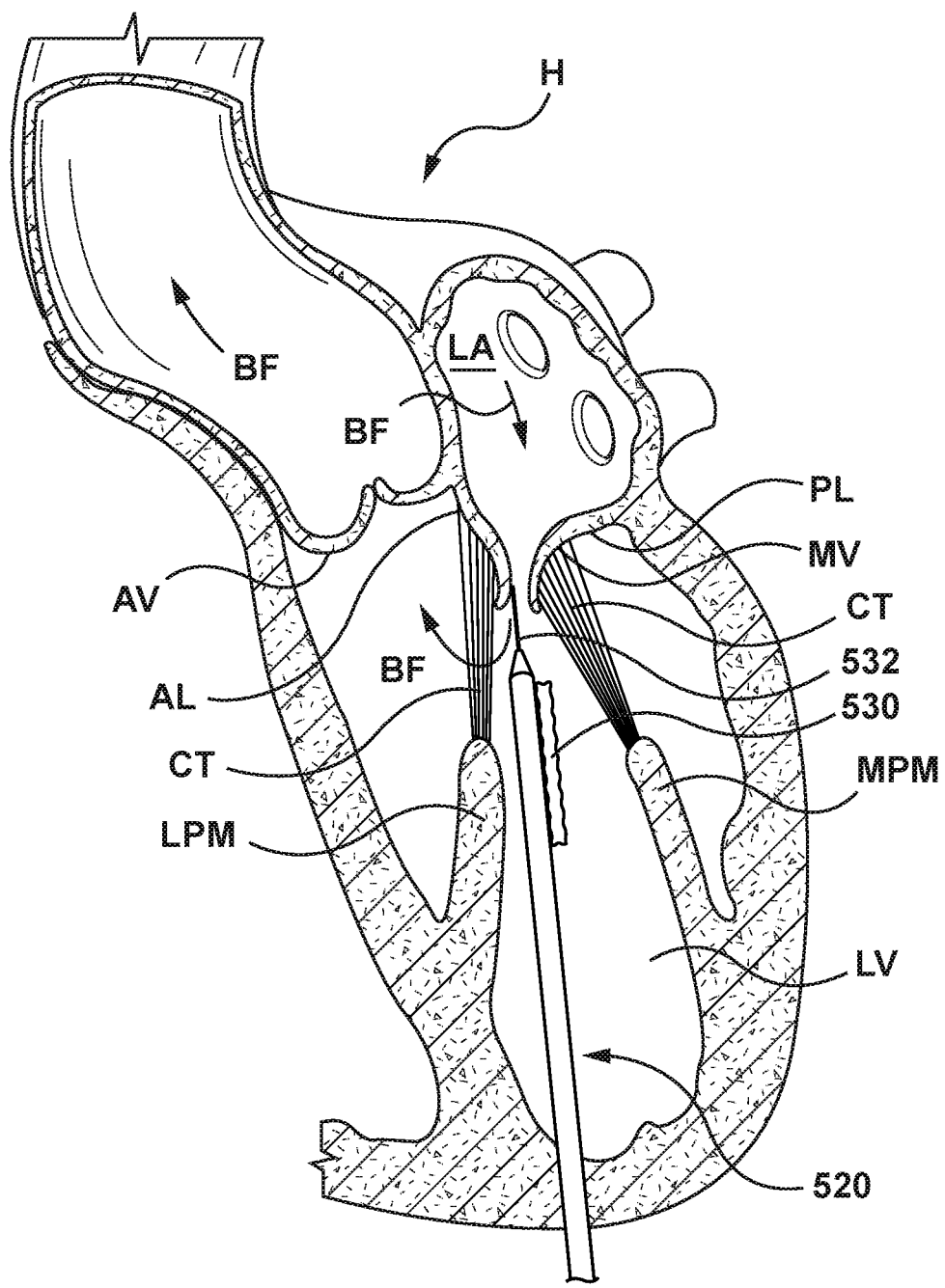
FIG. 18 is an illustration of the chordae management catheter of FIG. 5 in situ, the chordae management catheter being positioned into the left ventricle via a transapical approach, wherein the displacement component of the chordae management catheter is in a delivery or unexpanded configuration.

A method of delivering a valve prosthesis to an annulus of a native valve of a heart, the native valve having chordae tendineae, with the use of chordae management catheter 520 will now be described with reference to FIGS. 18-22. With reference to FIG. 18, chordae management catheter 520 is depicted in situ after being tracked over a guidewire 532, with a displacement component 530 thereof in a delivery or unexpanded configuration. In this embodiment, the chordae management catheter is positioned into the left ventricle via a transapical approach and positioning chordae management catheter 520 within the left ventricle of the heart includes introducing the catheter into the apex of the heart as well as introducing the catheter through a ventricular wall adjacent to the apex of the heart. Stated another way, "transapical approach" as used herein is not limited to introduction via only the apex of the heart but also includes the ventricular wall adjacent to the apex of the heart since the anatomy of a heart may vary from patient to patient. Further, as noted above, although described in FIG. 18 as being introduced into the left ventricle for treatment of chordae tendineae associated with a native mitral valve, chordae management catheter 520 may be similarly introduced into the right ventricle for treatment of chordae tendineae associated with a native tricuspid valve. Chordae management catheter 520 is maneuvered and advanced until the distal tip thereof is positioned in the left ventricle below the annulus of the native mitral valve, i.e., the underside of the native mitral valve. In another embodiment, chordae management catheter 520 is maneuvered and advanced until displacement component 530 engages or contacts the underside of the native mitral valve. Chordae management catheter 520 may be tracked over guidewire 532, which may be removed after the catheter is positioned as desired.

Figure 19:
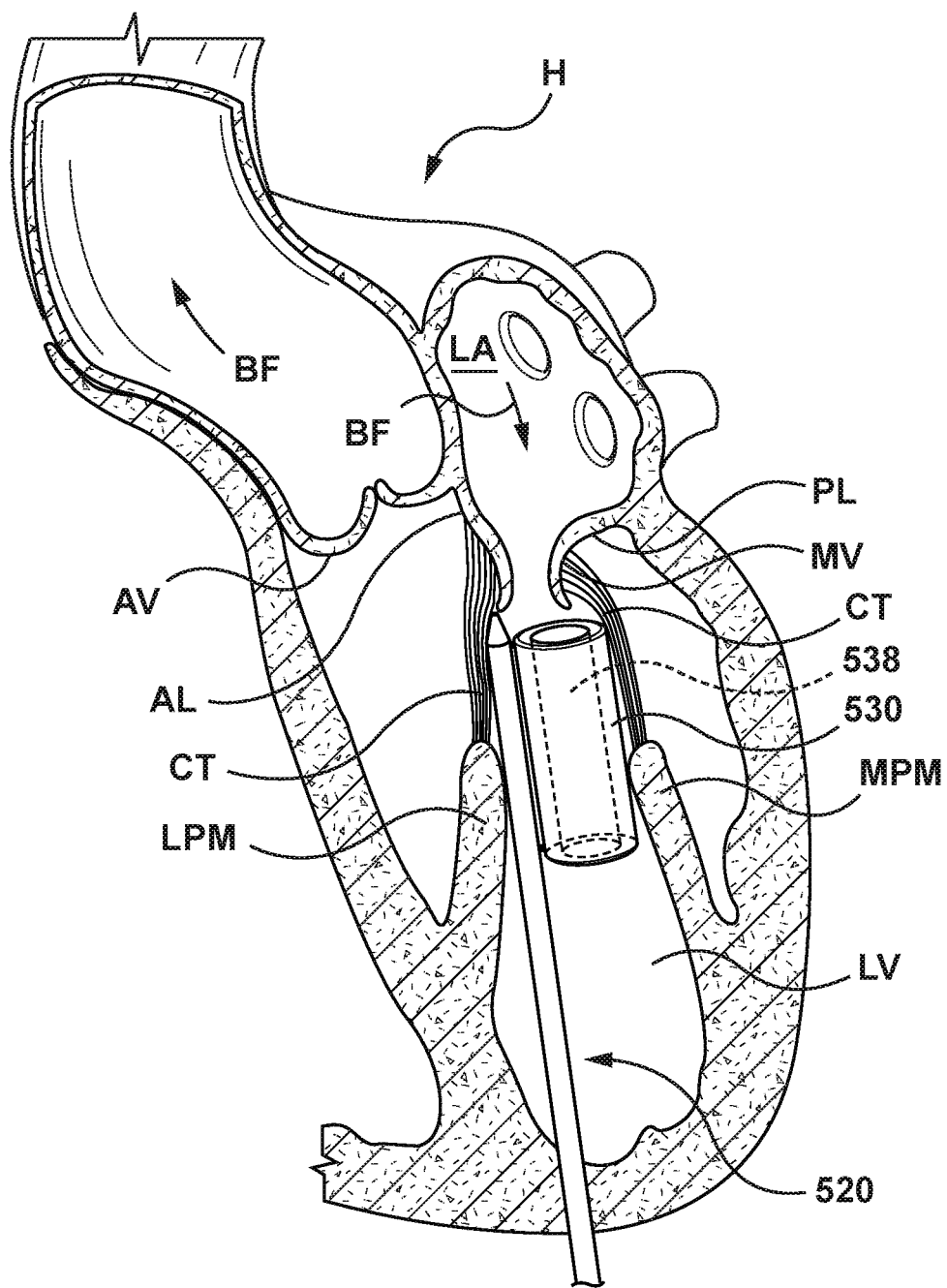
FIG. 19 is an illustration of the chordae management catheter of FIG. 5 in situ, wherein the displacement component of the chordae management catheter is in a deployed or expanded configuration.

Once displacement component 530 is positioned within the left ventricle as described, displacement component 530 is inflated to a deployed or expanded configuration as shown in FIG. 19. Displacement balloon 530 is inflated within the ventricle to push all chordae tendineae, trabeculae and ventricular bands radially outwards towards the ventricular wall. Displacement of the chordae tendineae does not damage the chordae tendineae, but rather central opening 538 of displacement component 530 provides an unobstructed channel or pathway to the native mitral valve. In an embodiment hereof, displacement component 530 may be inflated with an endoinflater (not shown) as will be understood by one of ordinary skill in the art. Displacement component 530 may be fully inflated or expanded, or may be only partially inflated or expanded as required to push all chordae tendineae, trabeculae and ventricular bands radially outwards towards the ventricular wall. The width and length of displacement component 530 relative to the size of the left ventricle may vary from that depicted in FIG. 19. For example, the expanded or inflated displacement component may be configured to have a longer length than shown so it extends from the underside of the native mitral valve to the base of the left ventricle, or may be configured to have a shorter length than shown such as the annular donut-shaped configuration of FIG. 11. Similarly, the expanded or inflated displacement component may be configured to have a greater width than shown so it essentially fills the left ventricle and pushes the papillary muscles radially outward towards and against the ventricular wall. The dimensions vary according to application and are only required to be configured to push chordae tendineae outwards enough provide to an unobstructed channel or pathway to the native mitral valve.

Figure 20:
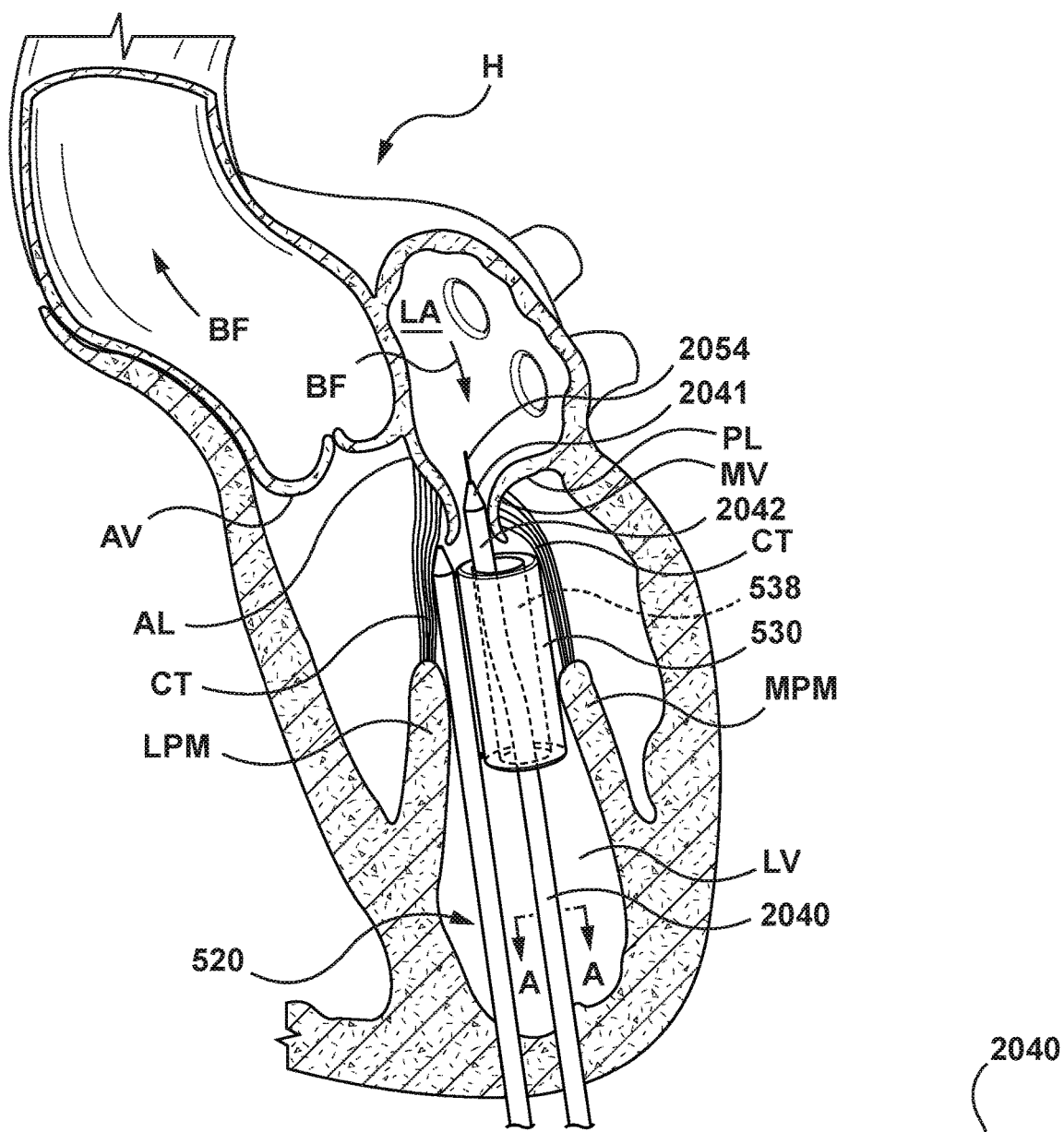
FIG. 20 is an illustration of a valve delivery system being positioned through the chordae management catheter of FIG. 5 in situ, the valve delivery system being positioned into the left ventricle via a transapical approach, wherein the displacement component of the chordae management catheter is in a deployed or expanded configuration and a valve prosthesis of the valve delivery system is in a delivery or unexpanded configuration.

Once displacement component 530 is positioned and expanded within the left ventricle to displace the chordae tendineae, a valve delivery system 2040 having valve prosthesis 101 mounted thereon is delivered to the treatment site and advanced through central opening 538 of expanded displacement component 530 as shown on FIG. 20. Valve delivery system 2040 is depicted in situ after being advanced within the central opening of the displacement component, with valve prosthesis 101 in a delivery or unexpanded configuration. In this embodiment, valve delivery system 2040 is positioned into the left ventricle via a transapical approach and positioning valve delivery system 2040 within the left ventricle of the heart includes introducing the catheter into the apex of the heart as well as introducing the catheter through a ventricular wall adjacent to the apex of the heart. Stated another way, as described previously herein, "transapical approach" as used herein is not limited to introduction via only the apex of the heart but also includes the ventricular wall adjacent to the apex of the heart since the anatomy of a heart may vary from patient to patient. Further, as noted above, although described in FIG. 20 as being introduced into the left ventricle for valve replacement of a native mitral valve, valve delivery system 2040 may be similarly introduced into the right ventricle for valve replacement of a native tricuspid valve. Valve delivery system 2040 is maneuvered and advanced through central lumen 538 of the inflated displacement component 530 towards the annulus of the native mitral valve of the heart.

Figure 20A:
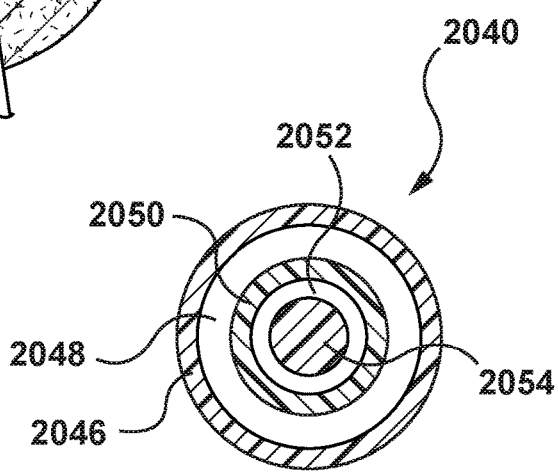
FIG. 20A is a cross-sectional view taken along line A-A of FIG. 20.

In FIG. 20, valve delivery system 2040 is depicted with valve prosthesis 101 (obstructed in FIG. 20 but shown in FIG. 22) in a delivery or compressed configuration in which the valve prosthesis is loaded within a distal capsule section 2042 of the valve delivery system. Valve delivery system 2040 is configured for transcatheter repair/replacement of a defective heart valve. As shown in FIG. 20A, valve delivery system 2040 also includes a tubular shaft component 2046 defining a lumen 2048 therethrough and a tubular inner shaft 2050 defining a lumen 2052 therethrough. A distal tip 2041 is coupled to a distal end of inner shaft 2050. Inner shaft 2050 is concentrically disposed within lumen 2048 of shaft component 2046, and lumen 2052 of inner shaft 2050 is sized to slidingly receive a guidewire 2054 such that valve delivery system 2040 is configured to be tracked over the guidewire during delivery of the valve prosthesis if desired, although tracking over a guidewire is not required since valve delivery system 2040 is advanced through central lumen 538 of the inflated displacement component 530. In the delivery configuration of FIG. 20, distal capsule section 2042 is disposed over the valve prosthesis to compressively retain the valve prosthesis in crimped engagement with inner shaft 2050. Valve delivery system 2040 may be one of, but is not limited to, the delivery systems described in U.S. Pat. No. 9,034,032 to McLean et al. previously incorporated by reference in its entirety, U.S. Patent Publication No. 2011/0245917 to Savage et al., U.S. Patent Publication No. 2011/0251675 to Dwork, U.S. Patent Publication No. 2011/0251681 to Shipley et al., U.S. Patent Publication No. 2011/0251682 to Murray, III et al., and U.S. Patent Publication No. 2011/0264202 to Murray, III et al., each of which is herein incorporated by reference in its entirety. Distal tip 2041 of valve delivery system 2040 is advanced beyond the native valve annulus and located within the left atrium.

Figure 21:
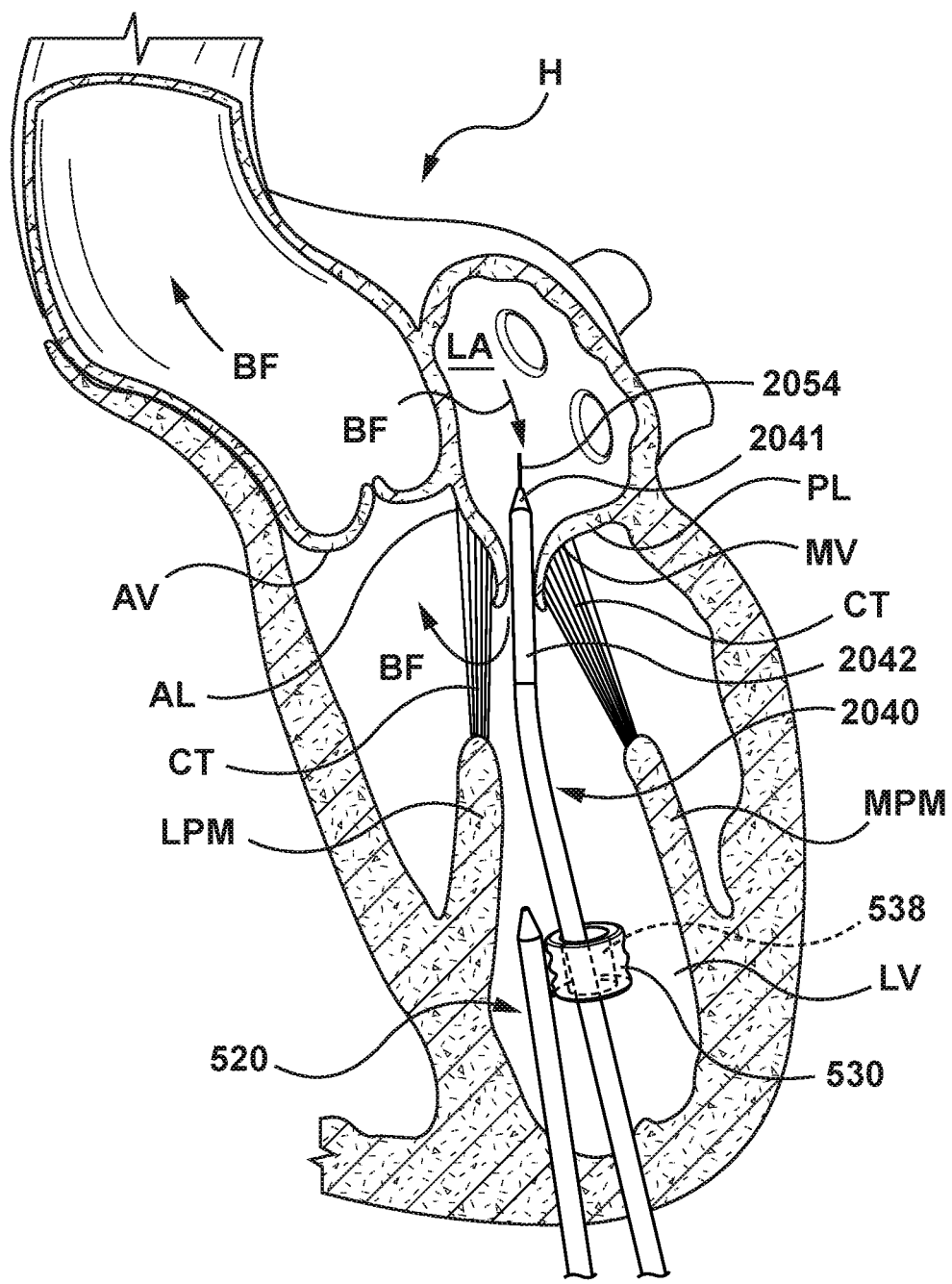
FIG. 21 is an illustration of a valve delivery system being positioned through the chordae management catheter of FIG. 5 in situ, wherein the displacement component of the chordae management catheter is in at least a partially unexpanded configuration and the chordae management catheter has been at least partially proximally retracted or withdrawn.
Figure 22:
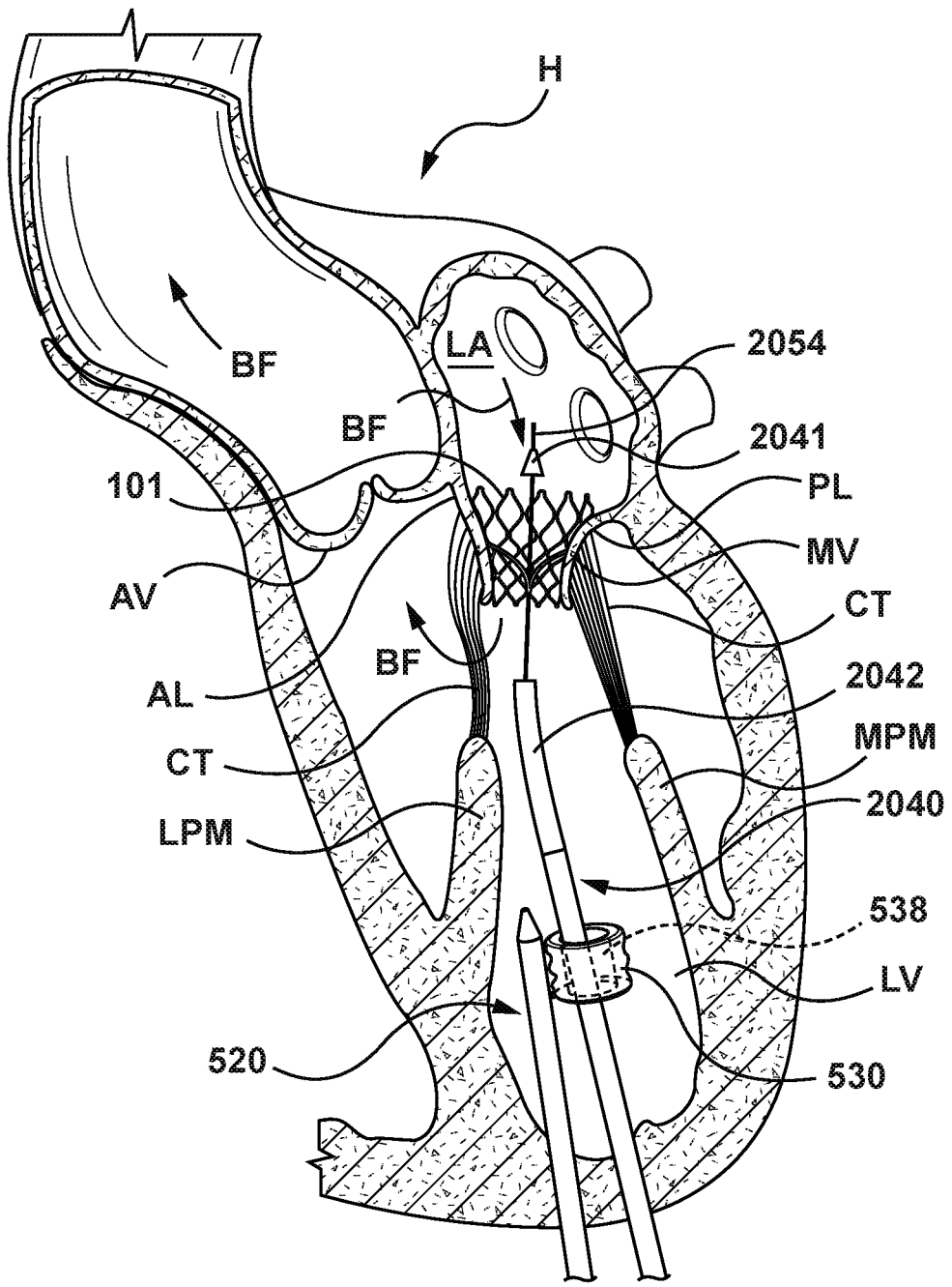
FIG. 22 is an illustration of the valve prosthesis of FIG. 1 being deployed in situ after at least partial removal of the chordae management catheter.

After valve delivery system 2040 is positioned as desired, displacement component 530 is at least partially deflated or unexpanded and chordae management catheter 520 is at least partially proximally withdrawn or retracted as shown in FIG. 21. Chordae management catheter 520 is at least partially proximally withdrawn or retracted in order to avoid interfering with delivery of valve prosthesis 101. After chordae management catheter 520 is at least proximally withdrawn, valve prosthesis 101 is fully deployed or expanded as shown in FIG. 22. More particularly, distal capsule section 2042 of valve delivery system 2040 is proximally retracted to expose and release the entire length of valve prosthesis 101. Valve prosthesis 101 self-expands into apposition with the surrounding native anatomy, i.e., with the annulus of the native valve. Valve delivery system 2040 may then be proximally retracted through central lumen 538 of the partially deflated or deflated displacement component 530 and removed, followed by complete deflation of displacement component 530 and removal of chordae management catheter 520.

In another embodiment hereof, the valve prosthesis is fully deployed prior to deflating and retracting the displacement component. More particularly, if inflated displacement component 530 is positioned so as not to interfere with deployment of valve prosthesis 101, valve prosthesis 101 may be fully deployed with chordae management catheter 520 and expanded displacement component 530 still in place. Valve delivery system 2040 may then be proximally retracted through central lumen 538 of the inflated displacement component 530 and removed, followed by deflation of displacement component 530 and removal of chordae management catheter 520.

Figure 23:
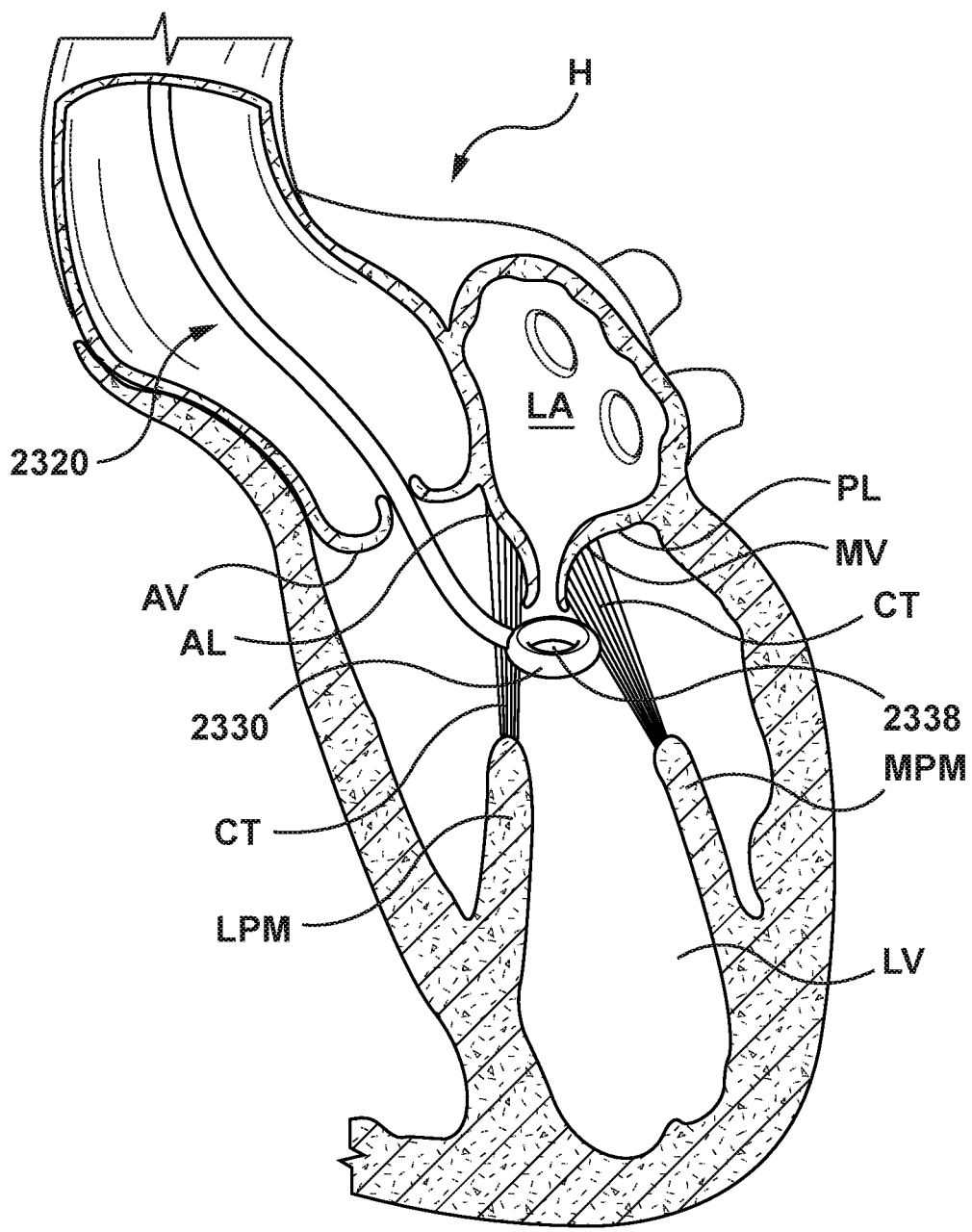
FIG. 23 is an illustration of a chordae management catheter in situ, the chordae management catheter being positioned into the left ventricle via a trans-aortic approach, wherein the displacement component of the chordae management catheter is in a delivery or unexpanded configuration.

Although described as being delivered transapically, chordae management catheter 520 and displacement component 530 may be delivered via an alternative access route. For example, FIG. 23 illustrates a chordae management catheter 2320 having a displacement component 2330 being positioned into the left ventricle via a transaortic approach. Displacement component 2330 is navigated through the aorta and into the left ventricle. Once positioned within the left ventricle, displacement component 2330 is inflated to displace the chordae tendeneae and a valve delivery system (not shown) is delivered transapically through a center lumen 2338 of displacement component 2330 as described above. To position chordae management catheter 2320 into the left ventricle via a transaortic approach as shown in FIG. 23, in accordance with techniques known in the field of interventional cardiology and/or interventional radiology, chordae management catheter 2320 is transluminally advanced in a retrograde approach through the vasculature to a native aortic valve AV that extends between a patient's left ventricle LV and a patient's aorta A. Delivery of chordae management catheter 2320 to the native aortic valve AV is accomplished via a percutaneous transfemoral approach in which the delivery system is tracked through the femoral artery, up the aorta and around the aortic arch in order to access the native aortic valve AV. Chordae management catheter 2320 is further delivered to the left ventricle by passing chordae management catheter 2320 through the native aortic valve AV and into the left ventricle.

Figure 24:
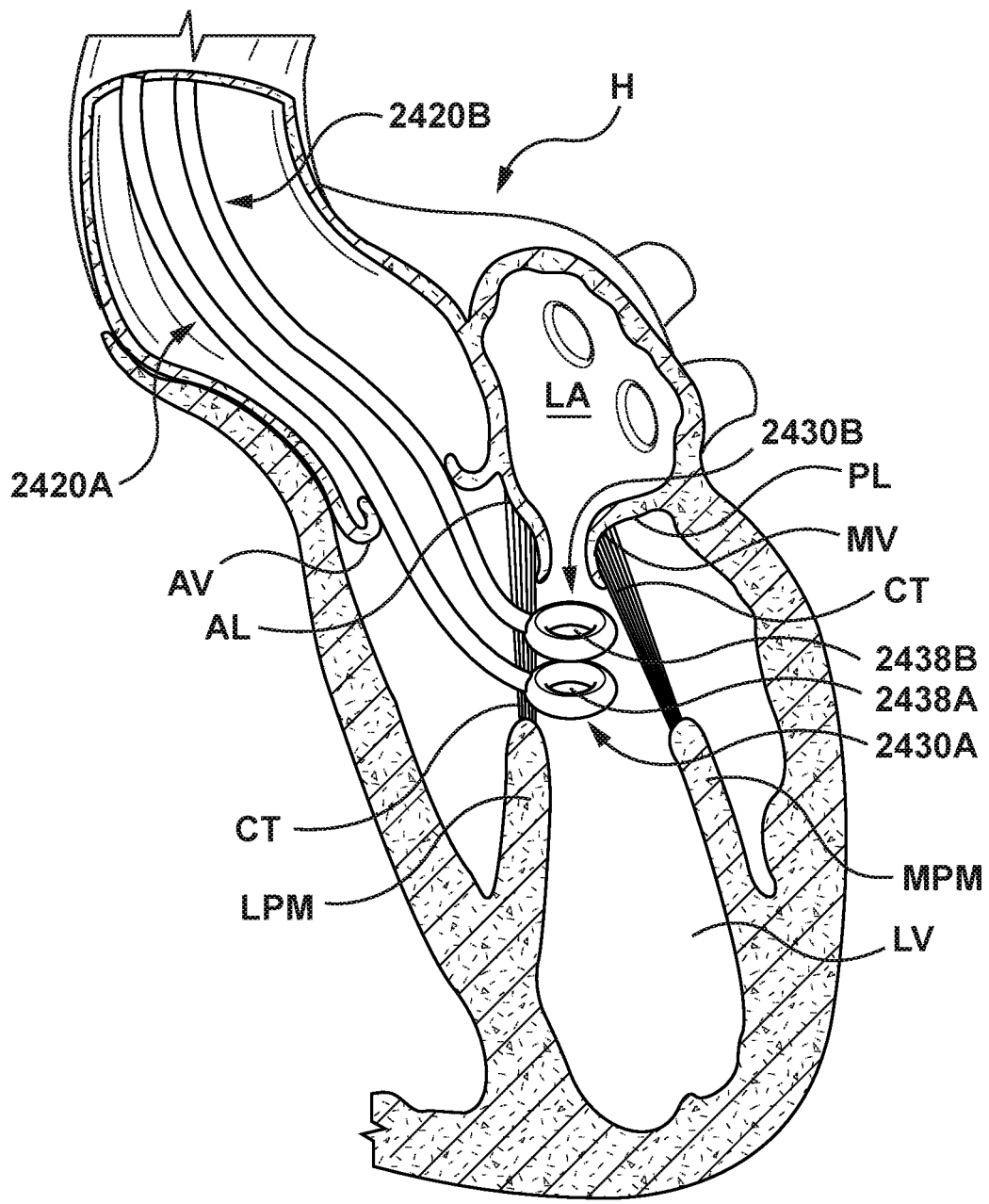
FIG. 24 is an illustration of two chordae management catheters in situ, the chordae management catheters being sequentially positioned into the left ventricle via a transaortic approach, wherein the displacement components of the chordae management catheters are in expanded or inflated configurations.

The use of multiple displacement components may result in even greater chordae tendineae management. With reference to FIG. 24, two chordae management catheters 2420A, 2420B are sequentially positioned into the left ventricle via a transaortic approach. Each catheter 2420A, 2420B includes a displacement component 2430A, 2430B that is similar displacement component 1130 having a donut-shaped or toroid-shaped configuration. Chordae management catheters 2420A, 2420B are positioned so that displacement components 2430A, 2430B are longitudinally and circumferentially aligned. Both displacement components are inflated within the ventricle to push chordae tendineae radially outward. Once both displacement components 2430A, 2430B are inflated, a valve delivery system (not shown) is delivered transapically through a center lumen 2438A of inflated displacement component 2430A as well as through a center lumen 2438B of inflated displacement component 2430B.

Figure 25:
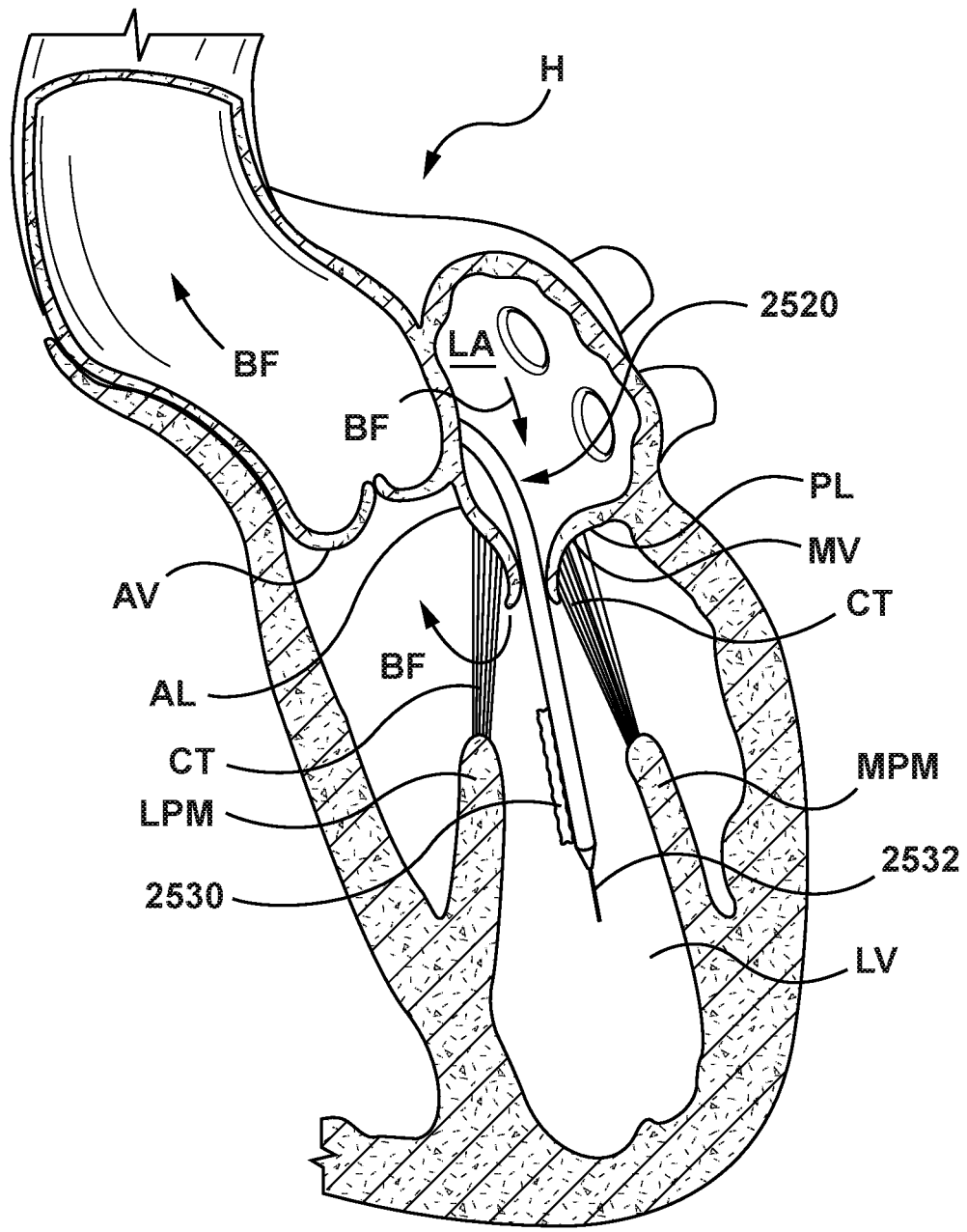
FIG. 25 is an illustration of a chordae management catheter in situ, the chordae management catheter being positioned into the left ventricle via a trans-septal approach, wherein the displacement component of the chordae management catheter is in a delivery or unexpanded configuration.

FIG. 25 illustrates another alternative access route in that a chordae management catheter 2520 having a displacement component 2530 may be positioned into the left ventricle via a transseptal approach. Displacement component 2530 is navigated into the left atrium via the atrial septum and into the left ventricle. Once positioned within the left ventricle, displacement component 2530 is inflated to displace the chordae tendeneae and a valve delivery system (not shown) is delivered transapically through the center lumen 2538 of displacement component 2530 as described above. To position chordae management catheter 2520 into the left atrium via the atrial septum as shown in FIG. 25, in accordance with techniques known in the field of interventional cardiology and/or interventional radiology, chordae management catheter 2520 is shown after having been introduced into the vasculature via a percutaneous entry point, a.k.a the Seldinger technique, and having been tracked through the vasculature and into the left atrium. For example, the percutaneous entry point may be formed in a femoral vein. Thereafter, a guidewire 2532 is advanced through the circulatory system, eventually arriving at the heart. Guidewire 2532 is directed into the right atrium, traverses the right atrium and is made to puncture with the aid of a transeptal needle or pre-existing hole, the atrial septum, thereby entering the left atrium. Once guidewire 2532 is positioned, the endoluminal entry port and the atrial septum are dilated to permit entry of a guide catheter (not shown) and/or chordae management catheter 2520 into the left atrium. Thereafter, chordae management catheter 2520 is advanced into the left atrium through the punctured atrial septum and positioned through the mitral valve MV and into the left ventricle. Although not shown, it will be understood by those of ordinary skill in the art that chordae management catheter 2520 may be inserted into a guide catheter in order to be advanced through the atrial septum. In addition, although described as a transfemoral antegrade approach for percutaneously accessing the mitral valve, chordae management catheter 2520 may be positioned within the desired area of the heart via entry other different methods such as a transseptal antegrade approach via a thoracotomy for accessing the mitral valve.

FIGS. 26-38 illustrate another embodiment hereof in which a displacement component 2630 is a radially expandable funnel or conical component that relocates or displaces the chordae tendineae which interfere with mitral access from the apex, while a central lumen 2638 defined by displacement component 2630 provides a clear path or route for the valve delivery system to pass through to deploy the valve prosthesis and for the valve delivery system to be removed safely after valve deployment. Displacement component 2630 is configured to deploy within the left or right ventricle of a heart, displacing chordae tendineae and thereby clearing a pathway for a subsequently delivered valve delivery system which is advanced through central lumen or passageway 2638 defined by displacement component 2630. Displacement component 2630 is shown deployed in FIG. 26. Displacement component 2630 is a flat or planar element 2672 that is formed from a self-expanding material and shape-set in the deployed or expanded configuration shown best in FIG. 26, which may be described as a conical or funnel configuration or profile 2674. In an embodiment hereof, flat or planar element 2672 is a mesh formed from Nitinol or another self-expanding material. A distal circumferential end 2682 is wider than a proximal or opposing circumferential end 2681 of displacement component 2630, which is disposed within a distal end 2661 of an outer sheath 2660 of a chordae management catheter 2620 that will be described in more detail herein. Displacement component 2630 includes a first or inner longitudinal edge 2676 which has at least a proximal end thereof attached or secured to an intermediate shaft 2664 of chordae management catheter 2620 as will be described in more detail herein and also includes a second or outer longitudinal edge 2678 that is free or unattached to the chordae management catheter in this embodiment.

More particularly, with reference to FIGS. 27, 27A, and 27B, chordae management catheter 2620 having displacement component 2630 at a distal end thereof will now be described in more detail. Chordae management catheter 2620 includes outer shaft 2660 defining a lumen 2662 there-through and intermediate shaft 2664 defining a lumen 2666 there-through. Intermediate shaft 2664 is concentrically disposed within outer shaft 2660. Outer shaft 2660 is retractable and thus is movable in a longitudinal direction relative to intermediate shaft 2664. The length of intermediate shaft 2664 may vary. More particularly, intermediate shaft 2664 may distally extend up to distal circumferential end 2682 of displacement component 2630, in which case the full length of inner longitudinal edge 2676 may be attached to intermediate shaft 2664. However, intermediate shaft 2664 is only required to distally extend up to proximal circumferential end 2681 of displacement component 2630 so that at least a proximal end or portion of inner longitudinal edge 2676 may be attached or secured thereto. In the embodiment described herein, intermediate shaft 2664 distally extends up to proximal circumferential end 2681 of displacement component 2630 such that only a proximal end or portion of inner longitudinal edge 2676 is attached or secured thereto. FIG. 27B is a cross-sectional view taken along line B-B of FIG. 27 and depicts the approximate location of the distal end of intermediate shaft 2664, which may vary depending upon the desired length and dimensions of displacement component 2630.

During delivery of displacement component 2630, displacement component 2630 is compressed into a delivery configuration in which displacement component 2630 is enclosed or housed within lumen 2662 of outer shaft 2660 as shown in FIG. 27B. In the delivery configuration, a proximal end or portion of first or inner longitudinal edge 2676 is attached or secured to intermediate shaft 2664 of chordae management catheter 2620 via a bond 2680 or other attachment mechanism. Flat or planar element 2672 of displacement component 2630 is wrapped in a tight spiral within lumen 2662 of the chordae management catheter. When displacement component 2630 in its compressed or delivery configuration, flat or planar element 2672 winds in a series of one or more loops in a spiral fashion and consecutive or adjacent loops thereof are stacked against and contacting each other with substantially no space therebetween. At proximal circumferential end 2681 of displacement component 2630, which is secured to intermediate shaft 2664, flat or planar element 2672 of displacement component 2630 is wrapped in a tight spiral around intermediate shaft 2664. Stated another way, when the displacement component in a delivery configuration, proximal circumferential end 2681 of displacement component 2630 has a series of windings that extend around intermediate shaft 2664 such that each winding is enclosed between the outer and intermediate shafts.

Chordae management catheter 2620 may also include an inner shaft 2668 that defines a lumen 2669 there-through. Inner shaft 2668 includes a tapered distal tip 2670 attached to a distal end thereof, and inner shaft 2668 is slidingly received within lumen 2666 of intermediate shaft 2664 during delivery of displacement component 2630. Inner shaft 2668 is retractable and thus is movable in a longitudinal direction relative to intermediate shaft 2664. In an embodiment as shown in FIGS. 27, 27A, and 27B, inner shaft 2668 may define a guidewire lumen 2669 for slidingly receiving a guidewire 2632 so that chordae management catheter 2620 may be tracked over a guidewire during delivery thereof. Inner shaft 2668 is only utilized during delivery of displacement component 2630 as described with respect to FIGS. 41-43 therein. Once displacement component 2630 is deployed, inner shaft 2668 is proximally retracted and removed so that the valve delivery system may be advanced through lumen 2666 of intermediate shaft 2664.

Figure 26:
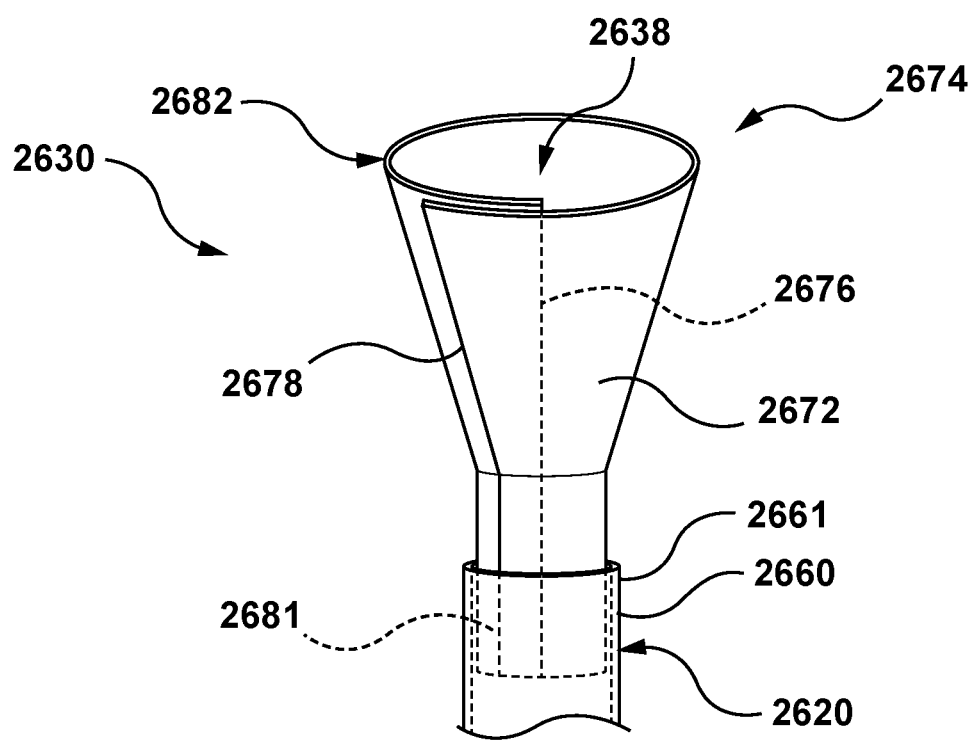
Figure 27:
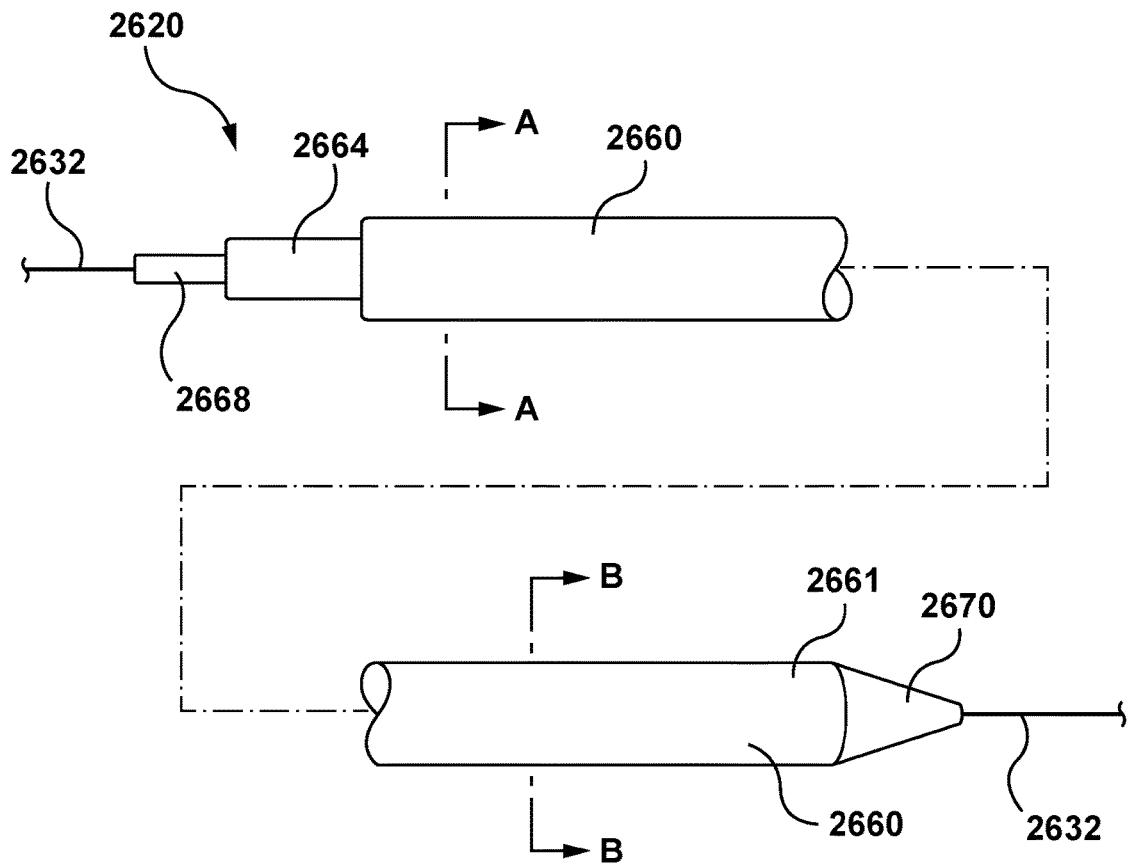
FIG. 27 is a side view of the chordae management catheter of FIG. 26, wherein an outer shaft of the chordae management catheter extends over the displacement component and thus the displacement component is in its delivery configuration.
Figures 27A, 27B:
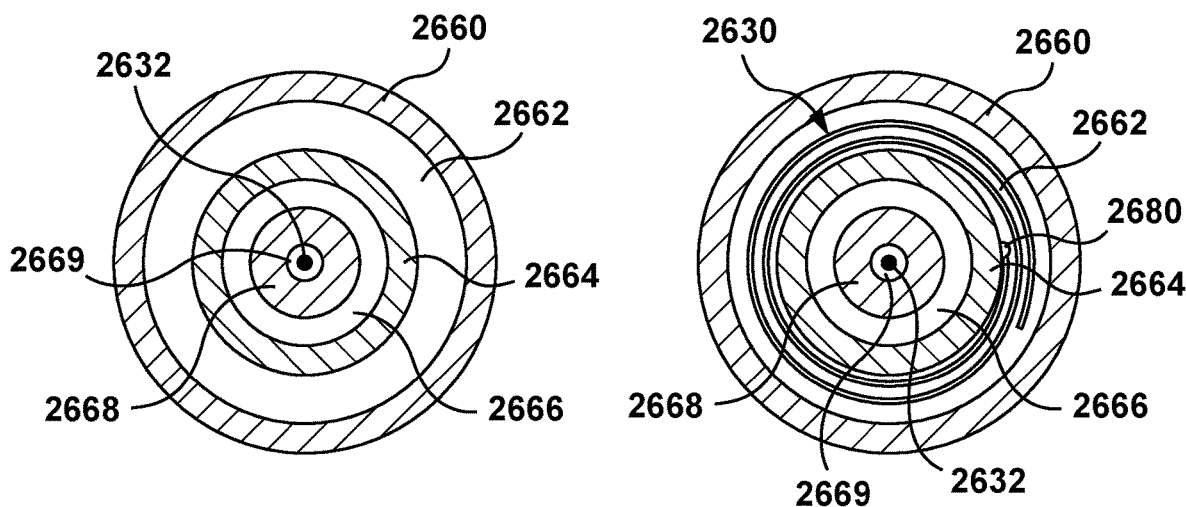
FIG. 27A is a cross-sectional view taken along line A-A of FIG. 27.
FIG. 27B is a cross-sectional view taken along line B-B of FIG. 27.
Figure 28:
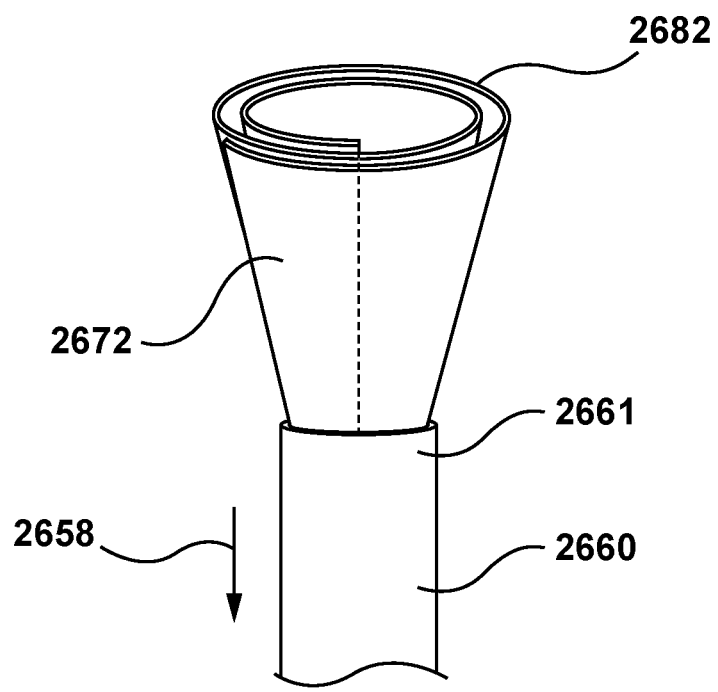
FIG. 28 is a perspective view of the displacement component of FIG. 26, wherein the outer shaft of the chordae management catheter is being retracted and the displacement component is in a partially deployed configuration.

During delivery of displacement component 2630, displacement component 2630 is housed within outer shaft 2660 as described above and outer shaft 2660 thus extends over the length of displacement component 2630 as shown in FIG. 27. When it is desired to deploy displacement component 2630, outer shaft 2660 is proximally retracted as indicated by directional arrow 2658 to expose displacement component 2630 and thereby permit displacement component 2630 to self-expand to its shape-set deployed or expanded configuration as shown in FIG. 28. FIG. 28 illustrates displacement component 2630 partially deployed, in the process of self-expanding and unfurling to its conical or funnel configuration or profile 2674. Outer shaft 2660 is retracted until nearly the full length of displacement component 2630 is exposed, although proximal circumferential end 2681 of displacement component 2630 remains disposed within outer shaft 2660 when displacement component 2630 is fully deployed as shown in FIG. 26 and described above. In order to retract or recapture displacement component 2630, outer shaft 2660 is distally advanced over displacement component 2630 which may be recaptured into the delivery configuration and housed within the outer shaft as described above with respect to FIGS. 27 and 27B.

Figure 29:
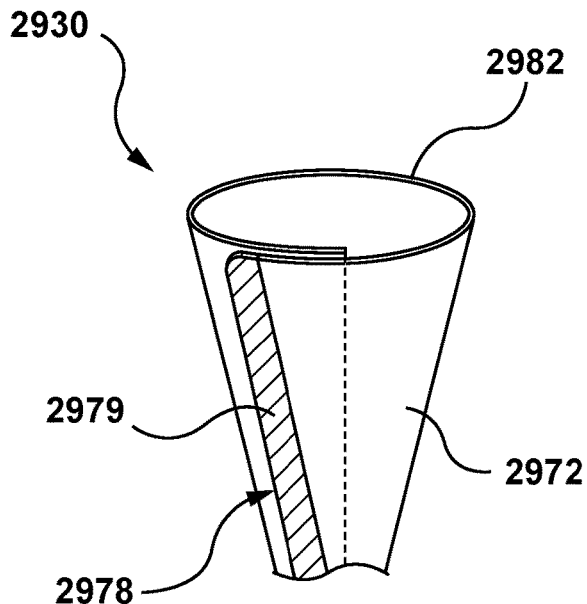
Figure 30:
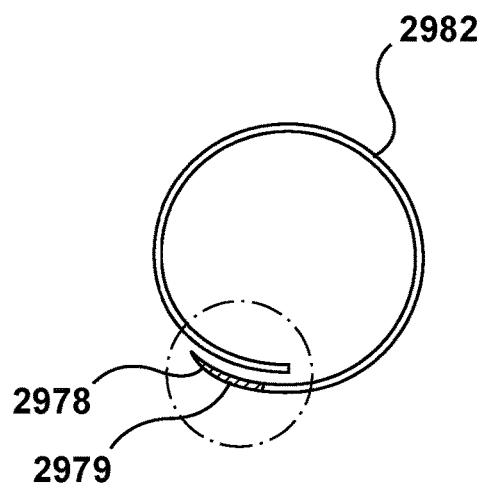
FIG. 30 is an end view of the displacement component of FIG. 29.
Figure 31:
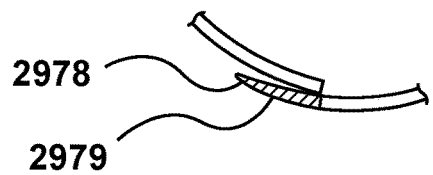
FIG. 31 is an enlarged view of a portion of FIG. 30, wherein the atraumatic longitudinal outer edge is rounded.

The second or outer longitudinal edge of displacement component 2630 that is free or unattached to the chordae management catheter may be rounded or tapered in order to be atraumatic. More particularly, FIG. 29 illustrates a displacement component 2930 similar to displacement component 2630 of FIG. 26 except that displacement component 2930 includes an atraumatic outer longitudinal edge 2978. Atraumatic outer longitudinal edge 2978 is formed from a different material 2979 than flat or planar element 2972 of displacement component 2930. For example, while flat or planar element 2972 is formed from a self-expanding material, atraumatic outer longitudinal edge 2978 is formed from a soft polymer having a durometer of 35 D or less. FIG. 30 illustrates an end view of distal circumferential end 2982 of displacement component 2930. As shown in the enlarged view of FIG. 31, material 2979 of atraumatic outer longitudinal edge 2978 may be tapered to the outer surface of flat or planar element 2972. In another embodiment, shown in the enlarged view of FIG. 32, material 3279 of atraumatic outer longitudinal edge 3278 may rounded.

Figure 33:
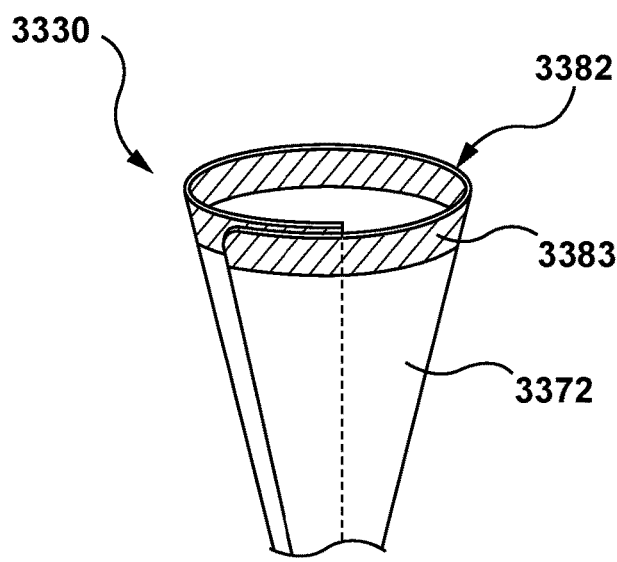
Figure 32:
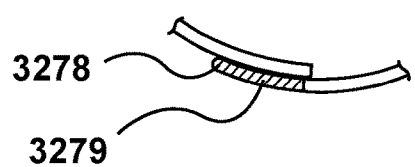
FIG. 32 is an enlarged view of a portion of FIG. 30 according to another embodiment hereof in which the atraumatic longitudinal outer edge is rounded.

In addition, the distal circumferential end of displacement component 2630 may be atraumatic. More particularly, FIG. 33 illustrates a displacement component 3330 similar to displacement component 2630 of FIG. 26 except that displacement component 3330 includes an atraumatic distal circumferential end 3382. Atraumatic distal circumferential end 3382 is formed from a different material 3383 than flat or planar element 3372 of displacement component 3330. For example, while flat or planar element 3372 is formed from a self-expanding material, atraumatic distal circumferential end 3382 is formed from a soft polymer having a durometer of 35 D or less.

Figure 34:
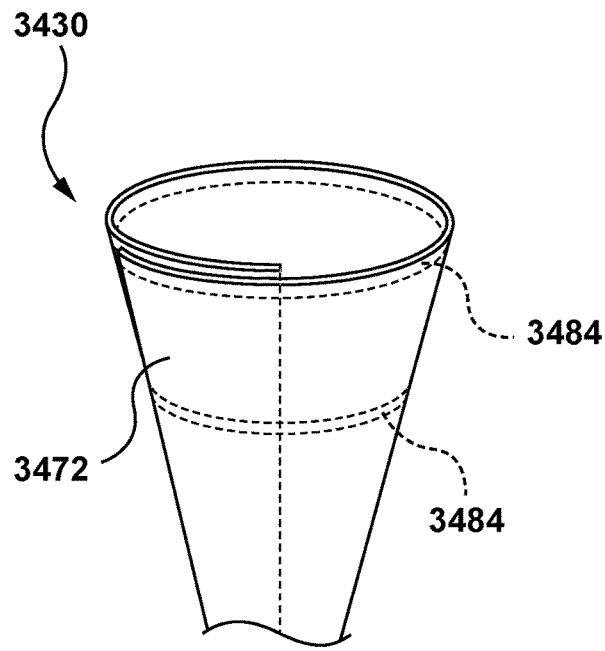
Figure 35:
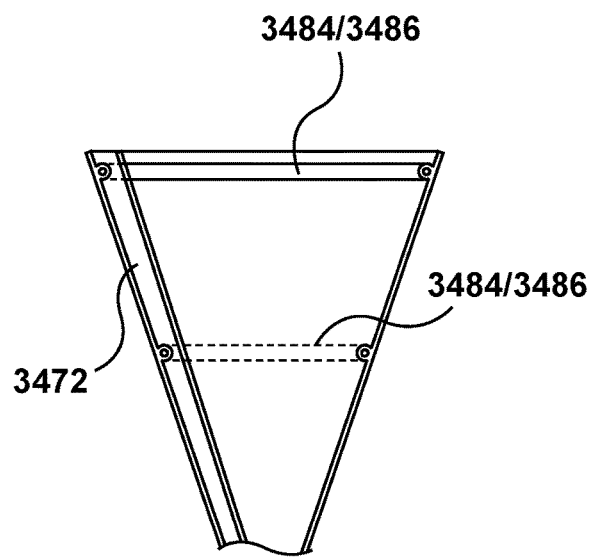
FIG. 35 is a sectional side view of FIG. 34.
Figure 36:
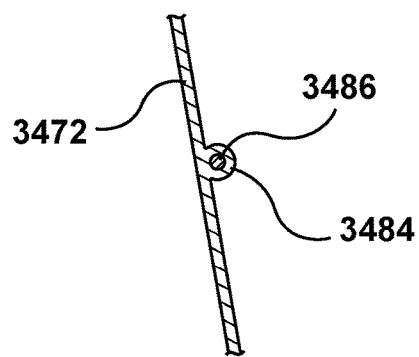
FIG. 36 is an enlarged view of a portion of FIG. 35.
Figure 37:
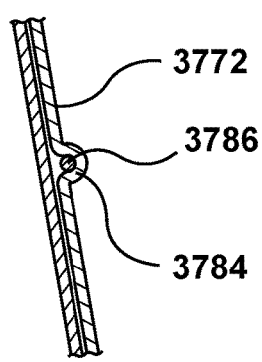
FIG. 37 is an enlarged view of a portion of FIG. 35 according to another embodiment hereof in which self-expanding filaments are received between two laminated sheets of the displacement component.
Figure 38:
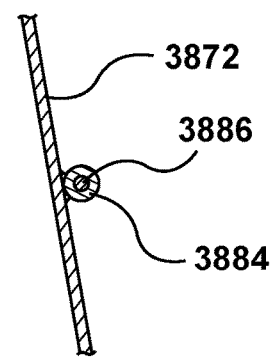
FIG. 38 is an enlarged view of a portion of FIG. 35 according to another embodiment hereof in which self-expanding filaments are received within tubular elements that form the circumferential passages.

Rather than constructing the entire flat or planar element of displacement component 2630 out of a self-expanding material, FIGS. 34-38 illustrate an embodiment in which Nitinol or self-expanding filaments 3486 are included within a displacement component 3430 to provide the displacement component with self-expanding properties. In FIG. 34, flat or planar element 3472 is formed from a non self-expanding material and includes circumferential channels or passageways 3484 formed therein. The non self-expanding material may be for example a polymer sheet such as polyurethane, HDPE, or nylon, a woven polymer, or a fibre polymer such as PTFE, HDPE, PTFE, nylon, or polyurethane. FIG. 34 illustrates two circumferential channels or passageways 3484 but a less or greater number of circumferential channels or passageways may be used. As shown in the side view and exploded view of FIGS. 35 and 36, respectively, self-expanding filaments 3486 are housed within circumferential channels or passageways 3484 to drive radial expansion of flat or planar element 3472. In an embodiment hereof depicted in FIG. 37, flat or planar element 3772 includes two laminated sheet layers to form circumferential channels or passageways 3784 for receiving self-expanding filaments 3786. In another embodiment hereof depicted in FIG. 38, circumferential channels or passageways 3884 are formed via tubular components that are attached to flat or planar element 3872, with the tubular components being configured to receive self-expanding filaments 3886.

FIGS. 39-43 illustrate an embodiment of a displacement component 3930 which is similar to displacement component 2630 except in the manner of deployment. Similar to displacement component 2630, displacement component 3930 is a radially expandable funnel or conical component that relocates or displaces the chordae tendineae which interfere with mitral access from the apex, while a central lumen 3938 defined by displacement component 3930 provides a clear path or route for the valve delivery system to pass through to deploy the valve prosthesis and for the valve delivery system to be removed safely after valve deployment. Displacement component 3930 is configured to deploy within the left or right ventricle of a heart, displacing chordae tendineae and thereby clearing a pathway for a subsequently delivered valve delivery system which is advanced through central lumen or passageway 3938 defined by displacement component 3930. Displacement component 3930 is shown in the deployed or expanded configuration in FIG. 39, which may be described as a conical or funnel configuration or profile 3974. Displacement component 3930 is a flat or planar element 3972 that is formed from a self-expanding material shape-set in the deployed or expanded configuration to assist in expansion thereof. A distal circumferential end 3982 is wider than a proximal or opposing circumferential end 3981 of displacement component 3930, which is disposed within a distal end 3961 of an outer sheath 3960 of a chordae management catheter 3920 that will be described in more detail herein. Displacement component 3930 includes a first or inner longitudinal edge 3976 that is attached or secured to intermediate shaft 3964 of chordae management catheter 3920 as will be described in more detail herein and also includes a second or outer longitudinal edge 3978 that is attached or secured to outer shaft 3960 of chordae management catheter 3920 as will be described in more detail herein.

Figure 40:
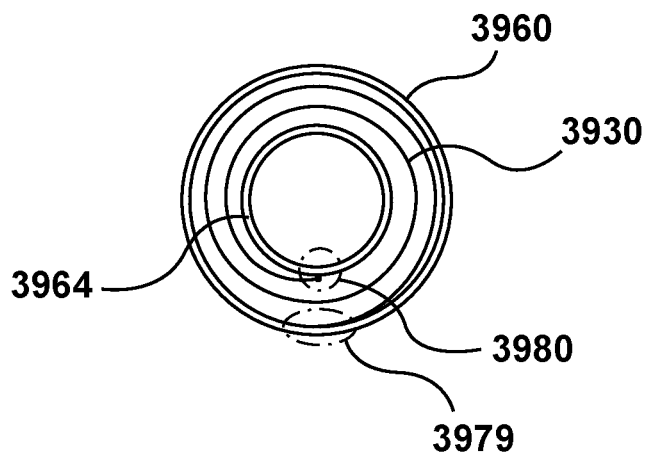
FIG. 40 is an end view of the displacement component and chordae management catheter of FIG. 39, wherein the displacement component is in its delivery configuration.

More particularly, with reference to the end view of FIG. 40, in this embodiment, chordae management catheter 3920 includes outer shaft 3960 and intermediate shaft 3964. Intermediate shaft 3964 is concentrically disposed within outer shaft 3960. Outer shaft 3960 is rotatable relative to intermediate shaft 3964 and/or intermediate shaft 3964 is rotatable relative to outer shaft 3960. During delivery of displacement component 3930, displacement component 3930 is in a delivery configuration in which displacement component 3930 is in a tightly-wound spiral that radially extends between outer shaft 3960 and intermediate shaft 3964, as shown in FIG. 40 which is an end view. Stated another way, an outermost surface of displacement component 3930 is in a delivery configuration is not greater than an outer diameter of outer shaft 3960. When displacement component 2930 in its compressed or delivery configuration, flat or planar element 2972 winds in a series of one or more loops in a spiral fashion and consecutive or adjacent loops thereof are stacked against and contacting each other with substantially no space therebetween. Notably, in this embodiment, displacement component 3930 is not housed or enclosed within a lumenal space of the chordae management catheter during delivery thereof but rather flat or planar element 3972 is exposed (with the exception of proximal circumferential end 3981 of displacement component 3930) and forms the distal end portion of chordae management catheter 3920 during delivery thereof. A proximal end of first or inner longitudinal edge 3976 is attached or secured to intermediate shaft 3964 of chordae management catheter 3920 via a bond 3980 or other attachment mechanism, and a proximal end of second or outer longitudinal edge 3978 is attached or secured to outer shaft 3960 of chordae management catheter 3920 via a bond 3979 or other attachment mechanism. Distal ends 3961, 3965 of outer and intermediate shafts 3960, 3664, respectively, are flush and are disposed adjacent to proximal circumferential end 3981 of displacement component 3930 during delivery.

Figure 39:
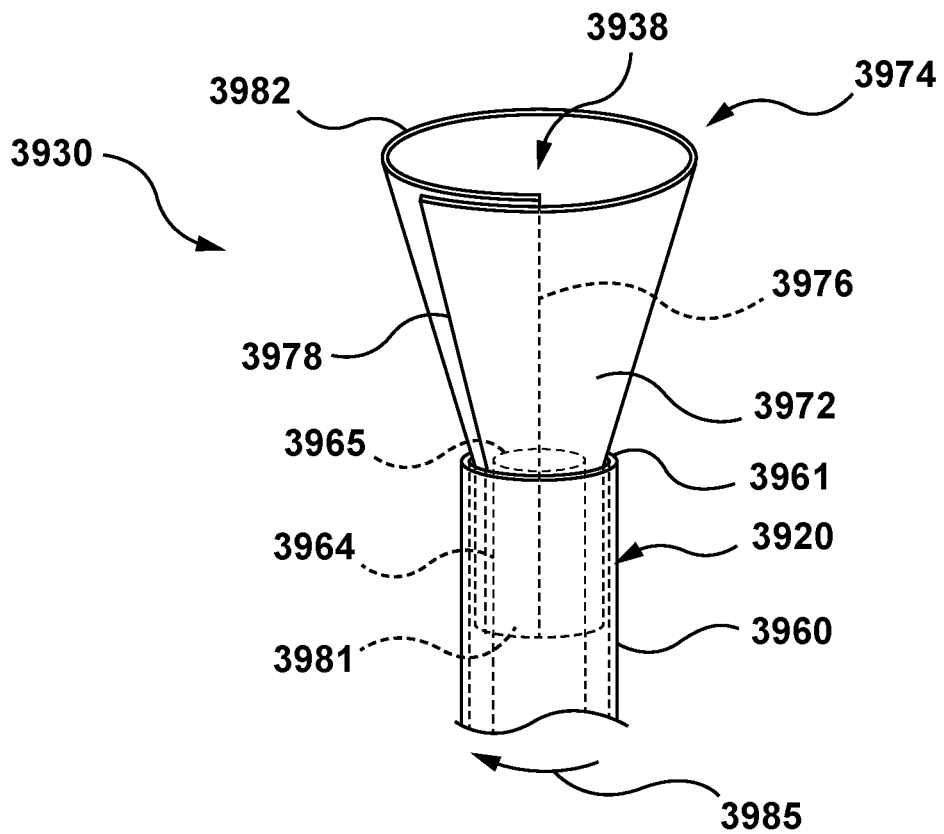

When it is desired to deploy or expand displacement component 3930, intermediate shaft 3964 is rotated or turned relative to outer shaft 3960 as indicated by directional arrow 3985 on FIG. 39. More particularly, intermediate shaft 3964 is rotated, first or inner longitudinal edge 3976 is rotated therewith and displacement component 3930 radially expands or unfurls to its conical or funnel configuration or profile 3974. In order to retract or recapture displacement component 3930, intermediate shaft 3964 is rotated in the opposite direction from directional arrow 3985. Displacement component 3930 may be recaptured or contracted to the tightly-wound spiral of the delivery configuration described above with respect to FIG. 40.

Although described herein that intermediate shaft 3964 is rotated or turned relative to outer shaft 3960 in order to expand displacement component 3930, relative rotation between intermediate shaft 3964 and outer shaft 3960 is all that is required so outer shaft 3960 may be rotated or turned relative to intermediate shaft 3964. However, if outer shaft 3960 is rotated in order to expand and contract displacement component 3930, outer shaft 3060 is rotated in the opposite direction from directional arrow 3985 to expand displacement component 3930 for deployment thereof and is rotated in the direction indicated by directional arrow 3985 to contract displacement component 3930 for recapture thereof.

Figure 41:
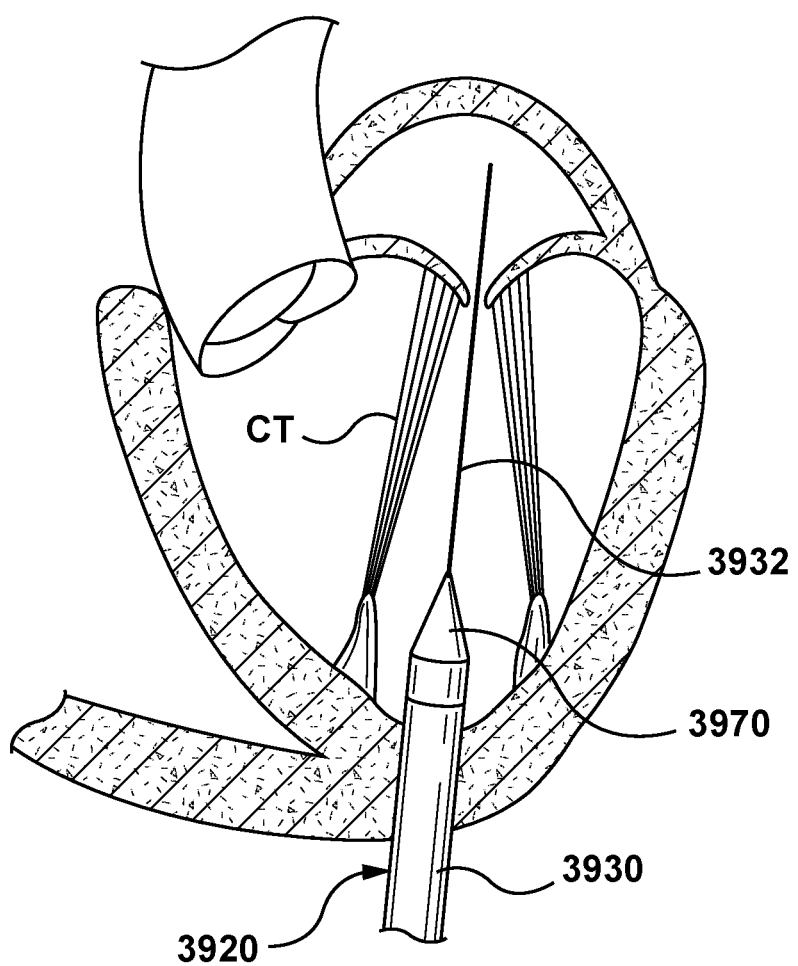
FIG. 41 is an illustration of the chordae management catheter of FIG. 39 in situ, the chordae management catheter being positioned into the left ventricle via a transapical approach, wherein the displacement component of the chordae management catheter is in a delivery or unexpanded configuration.
Figure 42:
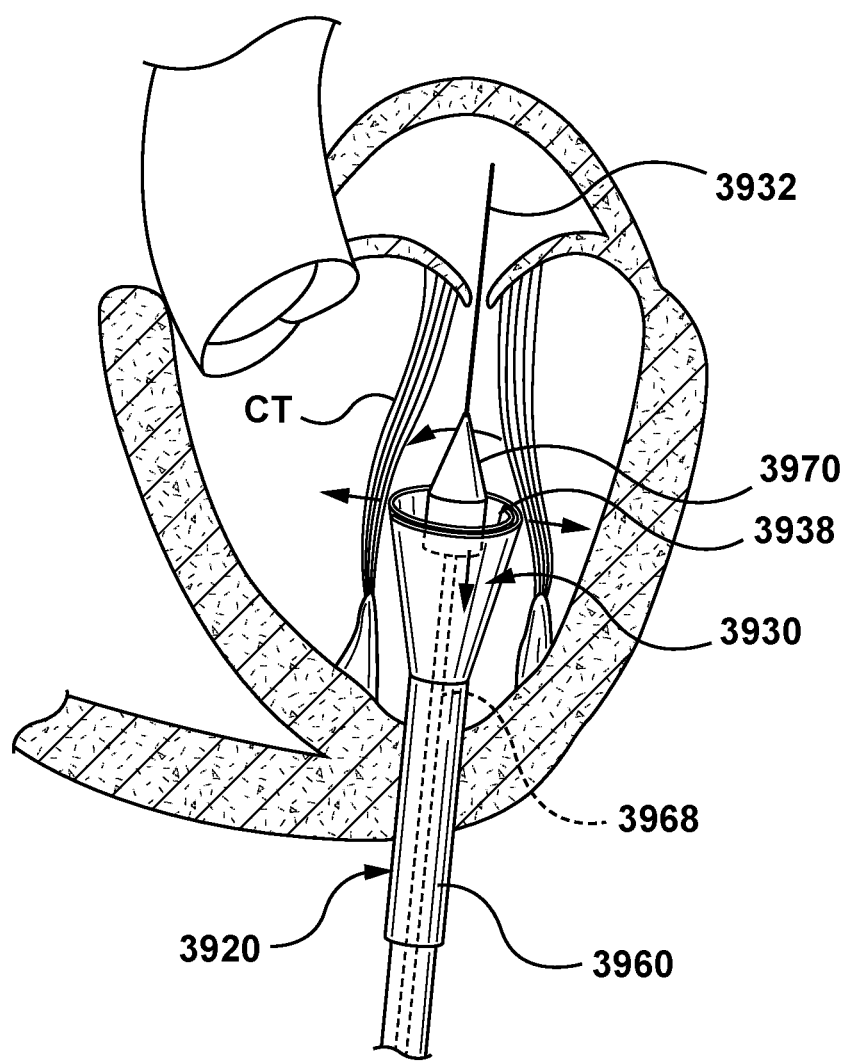
FIG. 42 is an illustration of the chordae management catheter of FIG. 39 in situ, wherein the displacement component of the chordae management catheter is in a deployed or expanded configuration.
Figure 43:
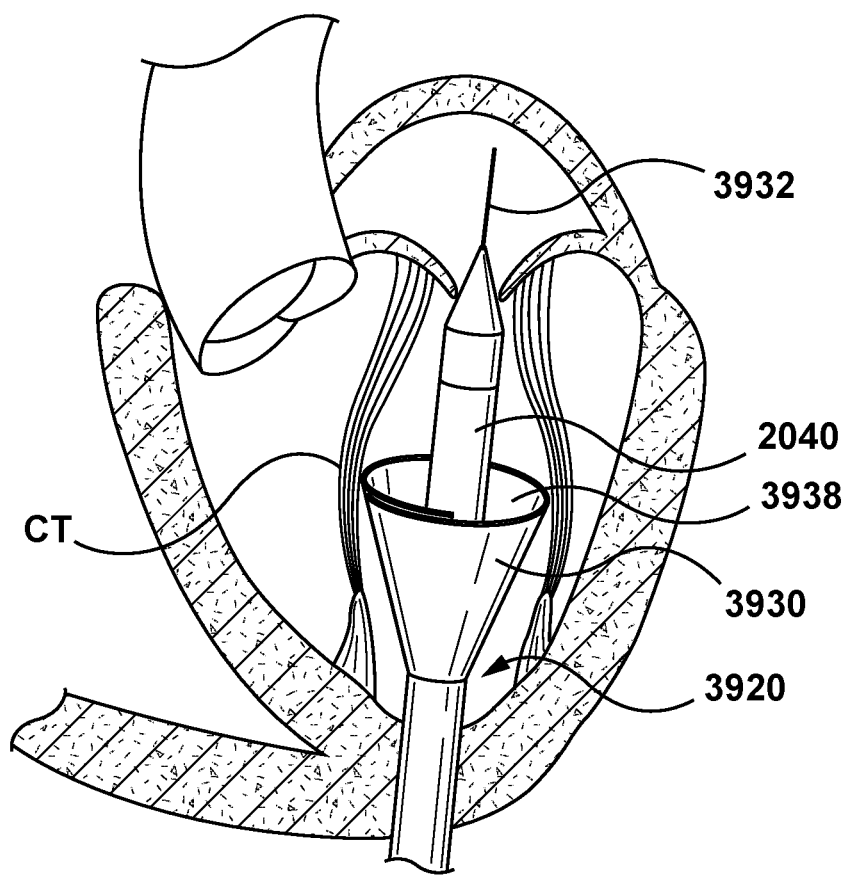
FIG. 43 is an illustration of a valve delivery system being positioned through the chordae management catheter of FIG. 39 in situ, the valve delivery system being positioned into the left ventricle via a transapical approach, wherein the displacement component of the chordae management catheter is in a deployed or expanded configuration and a valve prosthesis of the valve delivery system is in a delivery or unexpanded configuration.

Although not shown in FIGS. 39-40, chordae management catheter 3920 may also include an inner shaft 3968 similar to inner shaft 2668 described above. FIGS. 41-43 illustrate a method of use of chordae management catheter 3920 including inner shaft 3968. Inner shaft includes a tapered distal tip 3970 attached to a distal end thereof, and inner shaft 3968 is slidingly received within lumen 3966 of intermediate shaft 3964 during delivery of displacement component 3930 as shown in FIG. 41. Inner shaft 3968 may define a guidewire lumen (not shown in FIG. 41) for slidingly receiving a guidewire 3932 so that chordae management catheter 3920 may be tracked over a guidewire during delivery thereof as shown in FIG. 41.

More particularly, with reference to FIG. 41, chordae management catheter 3920 is depicted in situ after being tracked over a guidewire 3932, with a displacement component 3930 thereof in a delivery or unexpanded configuration in which it is exposed, in a tightly-wound spiral, and forms the distal end portion of chordae management catheter 3920. In this embodiment, the chordae management catheter is positioned into the left ventricle via a transapical approach and positioning chordae management catheter 3920 within the left ventricle of the heart includes introducing the catheter into the apex of the heart as well as introducing the catheter through a ventricular wall adjacent to the apex of the heart. Further, as noted above, although described in FIG. 41 as being introduced into the left ventricle for treatment of chordae tendineae associated with a native mitral valve, chordae management catheter 3920 may be similarly introduced into the right ventricle for treatment of chordae tendineae associated with a native tricuspid valve. Chordae management catheter 3920 is maneuvered and advanced until distal tip 3970 is positioned in the left ventricle below the annulus of the native mitral valve, i.e., the underside of the native mitral valve. In another embodiment, chordae management catheter 3920 is maneuvered and advanced until displacement component 3930 engages or contacts the underside of the native mitral valve. Chordae management catheter 3920 may be tracked over guidewire 3032, which may be removed after the catheter is positioned if desired.

Once displacement component 2930 is positioned within the left ventricle as described, displacement component 2930 is expanded or unfurled to a deployed or expanded configuration as shown in FIG. 42. Displacement component 2930 is expanded within the ventricle to push all chordae tendineae, trabeculae and ventricular bands radially outwards towards the ventricular wall. Displacement of the chordae tendineae does not damage the chordae tendineae, but rather central opening 3938 of displacement component 3930 provides an unobstructed channel or pathway to the native mitral valve. Displacement component 3930 may be fully inflated or expanded, or may be only partially inflated or expanded as required to push all chordae tendineae, trabeculae and ventricular bands radially outwards towards the ventricular wall. The width and length of displacement component 3930 relative to the size of the left ventricle may vary from that depicted in FIG. 42. For example, the expanded displacement component may be configured to have a longer length than shown so it extends from the underside of the native mitral valve to the base of the left ventricle. Similarly, the expanded displacement component may be configured to have a greater width than shown so it essentially fills the left ventricle and pushes the papillary muscles radially outward towards and against the ventricular wall. The dimensions vary according to application and are only required to be configured to push chordae tendineae outwards enough provide to an unobstructed channel or pathway to the native mitral valve. As described herein, deployment of displacement component 3930 occurs via relative rotation between intermediate shaft 3964 and outer shaft 3960. If displacement component 3920 is being utilized, deployment thereof occurs via proximal retraction of outer shaft 2660 as described herein.

Once displacement component 3930 is positioned and expanded within the left ventricle to displace the chordae tendineae, inner shaft 3968 with distal tip 3970 thereon is proximally retracted and removed, leaving outer shaft 3960, intermediate shaft 3964, and expanded displacement component 3930 in situ. As described with respect to inner shaft 2668, inner shaft 3968 is retractable and thus is movable in a longitudinal direction relative to intermediate shaft 3964. Once displacement component 3930 is deployed, inner shaft 3968 is proximally retracted and removed so that valve delivery system 2040 may be advanced through lumen 3966 of intermediate shaft 3964 as shown in FIG. 43.

More particularly, valve delivery system 2040 having valve prosthesis 101 mounted thereon is delivered to the treatment site and advanced through central opening 3938 of expanded displacement component 3930 as shown on FIG. 43. Valve delivery system 2040 is depicted in situ after being advanced within the central opening of the displacement component, with valve prosthesis 101 in a delivery or unexpanded configuration. In this embodiment, valve delivery system 2040 is positioned into the left ventricle via a transapical approach and positioning valve delivery system 2040 within the left ventricle of the heart includes introducing the catheter into the apex of the heart as well as introducing the catheter through a ventricular wall adjacent to the apex of the heart. Further, as noted above, although described in FIG. 43 as being introduced into the left ventricle for valve replacement of a native mitral valve, valve delivery system 2040 may be similarly introduced into the right ventricle for valve replacement of a native tricuspid valve. Valve delivery system 2040 is maneuvered and advanced through central lumen 3938 of the expanded displacement component 3930 towards the annulus of the native mitral valve of the heart. After valve delivery system 2040 is positioned as desired, valve prosthesis 101 may fully deployed or expanded as described in previous embodiments hereof. As long as expanded displacement component 3930 is positioned so as not to interfere with deployment of valve prosthesis 101, valve prosthesis 101 may be fully deployed with chordae management catheter 3920 and expanded displacement component 3930 still in place. Valve delivery system 2040 may then be proximally retracted through central lumen 3938 of expanded displacement component 3930 and removed, followed by recapture of displacement component 2430 and removal of chordae management catheter 3920.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of delivering a valve prosthesis to an annulus of a native valve of a heart, the native valve having chordae tendineae, the method comprising the steps of:

positioning a catheter within a ventricle of the heart, the catheter having a displacement component at a distal end thereof, wherein the displacement component defines a central lumen therethrough;

radially expanding the displacement component to push chordae tendineae within the ventricle radially outward;

introducing a valve delivery system into the ventricle of the heart, the valve delivery system having the valve prosthesis at a distal portion thereof, wherein the valve prosthesis is in a delivery configuration;

advancing the valve delivery system through the central lumen of the radially expanded displacement component towards the annulus of the native valve of the heart; and deploying the valve prosthesis into apposition with the annulus of the native valve.

2. The method of claim 1, wherein the displacement component is a balloon.

3. The method of claim 2, wherein the step of radially expanding the displacement component includes anchoring a distal end of the displacement component within the left atrium of the heart.

4. The method of claim 1, wherein the displacement component is a ring formed from a self-expanding material.

5. The method of claim 1, wherein the step of positioning the catheter within the ventricle of the heart includes introducing the catheter into the left ventricle via the apex of the heart.

6. The method of claim 1, wherein the step of positioning the catheter within the ventricle of the heart includes percutaneously advancing the catheter through the aorta and into the left ventricle.

7. The method of claim 1, wherein the step of positioning the catheter within the ventricle of the heart includes advancing the catheter transseptally into the left atrium and into the left ventricle.

8. The method of claim 1, further comprising the steps of:
radially collapsing the displacement component and at least partially removing the catheter prior to the step of deploying the valve prosthesis.

9. The method of claim 1, wherein the displacement component is a planar element shaped into a funnel configuration and at least partially formed from a self-expanding material.

10. The method of claim 1, wherein the step of radially expanding the displacement component includes retracting an outer shaft of the catheter to expose the displacement component.

11. The method of claim 10, wherein the step of radially expanding the displacement component includes rotating a shaft of the catheter.

12. A method of delivering a valve prosthesis to an annulus of a native valve of a heart, the native valve having chordae tendineae, the method comprising the steps of:
positioning a catheter within a ventricle of the heart, the catheter having a displacement component at a distal end thereof and the displacement component being in a delivery configuration during the step of positioning the catheter, wherein the displacement component defines a central lumen therethrough and is at least partially formed from a self-expanding material;

radially expanding the displacement component from the delivery configuration to an expanded configuration to push chordae tendineae within the ventricle radially outward, wherein the displacement component in the expanded configuration has a funnel configuration in which a distal circumferential end thereof is wider than a proximal circumferential end thereof;

introducing a valve delivery system into the ventricle of the heart, the valve delivery system having the valve prosthesis at a distal portion thereof, wherein the valve prosthesis is in a delivery configuration;

advancing the valve delivery system through the central lumen of the radially expanded displacement component towards the annulus of the native valve of the heart; and deploying the valve prosthesis into apposition with the annulus of the native valve.

13. The method of claim 12, wherein radially expanding the displacement component includes retracting an outer shaft of the catheter to expose the displacement component and thereby permit the displacement component to self-expand to the expanded configuration.

14. The method of claim 12, wherein the step of positioning the catheter within the ventricle of the heart includes introducing the catheter into the left ventricle via the apex of the heart.

15. The method of claim 12, further comprising the steps of:
radially collapsing the displacement component and at least partially removing the catheter prior to the step of deploying the valve prosthesis.

16. The method of claim 12, wherein the step of radially expanding the displacement component includes rotating a shaft of the catheter and thereby cause the displacement component to radially expand to the expanded configuration.

17. The method of claim 12, wherein an outer longitudinal edge of the displacement component is not attached to the catheter and the outer longitudinal edge is formed from a polymer having a durometer of 35D or less.

18. The method of claim 12, wherein the distal circumferential end of the displacement component is formed from a polymer having a durometer of 35D or less.

19. The method of claim 12, wherein the displacement component includes a planar element and at least one filament attached to the planar element, the at least one filament being formed from the self-expanding material and the planar element being formed from a material that is not self-expanding.

20. The method of claim 19, wherein the planar element includes at least one channel formed therein for receiving the at least one filament.

* * * * *